US007745397B2

(12) United States Patent
Hardy et al.

(10) Patent No.: US 7,745,397 B2
(45) **Date of Patent: *Jun. 29, 2010**

(54) PEPTIDE USEFUL IN IMMUNOMODULATION

(75) Inventors: Britta Hardy, Tel Aviv (IL); Annat Raiter, Kfar Saba (IL); Leah Klapper, Givataim (IL)

(73) Assignees: CureTech Ltd., Yavne (IL); Mor-Research Applications Ltd., Petach Tikva (IL)

( * ) Notice: Subject to any disclaimer, the term of this patent is extended or adjusted under 35 U.S.C. 154(b) by 241 days.

This patent is subject to a terminal disclaimer.

(21) Appl. No.: 11/957,128

(22) Filed: Dec. 14, 2007

(65) Prior Publication Data

US 2008/0175855 A1 Jul. 24, 2008

Related U.S. Application Data

(60) Division of application No. 11/411,832, filed on Apr. 27, 2006, now Pat. No. 7,329,639, which is a continuation of application No. 10/821,283, filed on Apr. 9, 2004, now Pat. No. 7,122,372, which is a continuation of application No. PCT/IL02/00831, filed on Oct. 15, 2002.

(30) Foreign Application Priority Data

Oct. 15, 2001 (IL) .................................... 145926

(51) Int. Cl.
*C07K 14/00* (2006.01)

(52) U.S. Cl. .......................................... 514/2; 530/350

(58) Field of Classification Search ...................... None
See application file for complete search history.

(56) References Cited

U.S. PATENT DOCUMENTS

| | | | |
|---|---|---|---|
| 4,457,917 A | 7/1984 | Schaller nee Kornmayer et al. | 424/177 |
| 4,900,549 A | 2/1990 | De Vries et al. | 424/88 |
| 5,164,372 A | 11/1992 | Matsuo et al. | 514/19 |
| 5,223,409 A | 6/1993 | Ladner et al. | 435/69 |
| 5,298,246 A | 3/1994 | Yano et al. | 424/94.1 |
| 5,354,900 A | 10/1994 | Matsuo et al. | 514/12 |
| 5,403,484 A | 4/1995 | Ladner et al. | 435/235.1 |
| 5,418,219 A | 5/1995 | Ueda | 514/12 |
| 5,439,688 A | 8/1995 | Orsolini et al. | 424/489 |
| 5,571,698 A | 11/1996 | Ladner et al. | 435/69.7 |
| 5,716,637 A | 2/1998 | Anselem et al. | 424/450 |
| 5,733,877 A | 3/1998 | Sato et al. | 514/12 |
| 5,736,519 A | 4/1998 | Deigin et al. | 514/18 |
| 5,747,653 A | 5/1998 | Huergo et al. | 530/389.5 |
| 5,837,500 A | 11/1998 | Ladner et al. | 435/69.7 |
| 5,877,155 A | 3/1999 | Miller et al. | 514/15 |
| 5,961,970 A | 10/1999 | Lowell et al. | 424/93.1 |
| 6,013,264 A | 1/2000 | Petre et al. | 424/227.1 |
| 6,306,404 B1 | 10/2001 | LaPosta et al. | 424/278.1 |
| 6,372,223 B1 | 4/2002 | Kistner et al. | 424/209.1 |
| 6,406,700 B1 | 6/2002 | Srivastava | 424/193.1 |
| 6,800,744 B1 | 10/2004 | Doucette-Stamm et al. | 536/23.1 |
| 6,833,447 B1 | 12/2004 | Goldman et al. | 536/23.1 |
| 7,329,639 B2 * | 2/2008 | Hardy et al. | 514/2 |

FOREIGN PATENT DOCUMENTS

| | | |
|---|---|---|
| WO | WO 94/20127 A1 | 9/1994 |
| WO | WO 95/11700 A1 | 5/1995 |
| WO | WO 95/19783 A1 | 7/1995 |
| WO | WO 95/20605 A1 | 8/1995 |
| WO | WO 97/11715 A1 | 4/1997 |
| WO | WO 00/06723 A1 | 2/2000 |
| WO | WO 00/58363 A1 | 10/2000 |

OTHER PUBLICATIONS

GenCore amino acid database, Accession No. A72330, Jun. 11, 1999.
Hardy, B. et al., "Activation of human lymphocytes by a monoclonal antibody to B lymphoblastoid cells; molecular mass and distribution of binding protein," Cancer Immunology Immunotherapy, vol. 40, No. 6, 376-382 (1995).
Hardy, B. et al., "Selection of novel peptides-based cancer vaccines by BAT monoclonal antibody," XP002370959, International Journal of Molecular Medicine, vol. 10, No. Supplement 1, p. S46; 7th World Congress on Advances in Oncology and the 5th International Symposium on Molecular Medicine; Hersonissos, Crete, Greece; Oct. 10-12, 2002.
Nelson et al., "Evidence for lateral gene transfer between Archaea and Bacteria from genome sequence of Thermotoga maritima," Nature 399: 323-329 (1999).
Raiter, A., "CD4$^+$ T lymphocytes as a primary cellular target for BAT mAb stimulation," International Immunology, vol. 12, No. 11, 1623-1628 (2000).
Ren et al., "Unique physiological and pathogenic features of Leptospira interrogans revealed a whole-genome sequencing," Nature 422: 888-893 (Apr. 2003).

* cited by examiner

*Primary Examiner*—Karen Cochrane Carlson
(74) *Attorney, Agent, or Firm*—Winston & Strawn LLP

(57) ABSTRACT

The present invention provides peptides and polynucleotides, and their use for immunomodulation, immunotherapy and vaccine particularly for anti-cancer therapy, and for diagnosis purposes. The immunomodulatory effect includes induction of proliferation and activation of peripheral blood lymphocytes and induction of an anti-tumor effect upon administration of peptides of the invention to subjects suffering from cancer.

14 Claims, 12 Drawing Sheets

| | Phage N52 | Phage N51 | Phage N40 | Phage N37 | Phage N6 | Phage N7 |
|---|---|---|---|---|---|---|
| □ O.D.450nm | 0.543 | 0.384 | 0.071 | 0.048 | 0.05 | 0.05 |

PEPTIDE USEFUL IN IMMUNOMODULATION

CROSS-REFERENCE TO RELATED APPLICATIONS

This application is a division of U.S. application Ser. No. 11/411,832 filed Apr. 27, 2006, now U.S. Pat. No. 7,329,639 B2, which is a continuation of U.S. application Ser. No. 10/821,283 filed Apr. 9, 2004, now U.S. Pat. No. 7,122,372, which is a continuation of International application PCT/IL02/00831 filed Oct. 15, 2002, the entire content of each of which is expressly incorporated herein by reference thereto.

FIELD OF THE INVENTION

The present invention relates to the field of immunotherapeutic vaccines and particularly the identification and use of peptides recognized by the immunomodulatory monoclonal antibodies designated BAT, to polynucleotides encoding these peptides, to pharmaceutical compositions comprising the peptides or the polynucleotides and to use thereof in immunomodulation, especially in anti-cancer therapy, and for diagnostic purposes.

BACKGROUND OF THE INVENTION

Cancer in its different forms is a major cause of death in humans. The most widely used therapeutic treatments of cancer are local therapy, such as surgery and radiation, or chemotherapy. The rapid increase of knowledge in recent years about the molecular and cellular bases of immune regulation, particularly at the level of T-cell responses, provides a new arsenal of immunotherapeutic approaches including the development of tumor vaccines. Tumor vaccine is administered for therapeutic or preventive purposes. This can include administration of immuno-potentiating agents as well as biological response modifiers such as interferons and interleukins, in order to stimulate the immune system.

Vaccination with an antigen molecule, such as a peptide or a protein, generally leads to an antibody response or CD4+ helper T cell response (Raychaudhuri et al., 1993 Immunol Today 14:344). This immune response is initiated by the binding of the antigen to selected major histocompatibility complex (MHC) molecules of either Class I or Class II. The latter molecules are expressed primarily on cells involved in initiating and sustaining immune responses such as T lymphocytes, B lymphocytes and macrophages. Class II molecules are recognized by CD4+ helper T cell and induce their proliferation and the amplification of the immune response to the epitope that is displayed. Class I MHC molecules are found on most nucleated cells and are recognized by cytotoxic T lymphocytes (CTLs) which destroy the antigen bearing cells. The CTL response is a major component of the immune system, active in immune surveillance and destruction of infected or malignant cells and invading organisms expressing foreign antigens on their surface. The ligand of the antigen-specific T lymphocyte receptor is a complex made up of a peptide fragment of a foreign antigen 8 to 10 amino acids in length, presented in the groove of MHC class I molecules. Unlike B cells, T cells do not recognize intact native antigen molecules. In general, cytotoxic T cell activation requires that the antigen be processed endogenously and cleaved into specific peptide fragments which are presented on the surface of antigen processing cells in association with class I MHC molecules.

Accordingly, a successful vaccine for cancer immunotherapy requires the identification of a target antigen and the production of a cytotoxic T cell response. Moreover, identification of cell surface antigens expressed exclusively or preferentially on certain tumors allows the formation of selective treatment strategies.

Numerous disclosures exist concerning immunomodulatory peptides. WO94/20127 discloses means and methods for selecting immunogenic peptides capable of specifically binding HLA-A2.1 allele and inducing T-cell activation. WO95/19783 relates to peptides based on an epitope derived from the product of the tumor associated gene MAGE-3. WO97/11715 discloses a peptide which mimics MUCI or other cancer peptides. WO00/06723 discloses tumor specific antigen peptides and use thereof as anti-tumor vaccines. U.S. Pat. No. 6,406,700 discloses methods for isolating immunogenic complexes by using a cDNA library from cancer cell RNA.

International patent applications WO95/20605 and WO00/58363 which are incorporated herein by reference, describe a novel monoclonal antibody designated BAT-1, also designated herein BAT, which induces lymphocyte proliferation and cytolytic activity against tumor target cells. A single intravenous administration of BAT into mice bearing various tumors resulted in striking anti-tumor effects manifested by regression of tumors and prolongation of survival. BAT also induced regression of human tumor xenografts transplanted into SCID mice that were engrafted with human peripheral blood lymphocytes. The anti-tumor activity of BAT is mediated by its immune stimulatory properties as was evident from adoptive transfer experiments in which splenocytes from BAT treated mice injected to mice bearing tumors induced regression of tumors. The membrane determinant recognized by BAT has not yet been identified or characterized.

Several alternative methods of identifying the peptide epitopes bound by monoclonal antibodies are recognized in the art. These methods include the use of phage display libraries such as disclosed in U.S. Pat. Nos. 5,223,409; 5,403,484; 5,571,698; 5,837,500 and continuations thereto. Phage display involves a selection technique enabling identification and isolation of a protein against a chosen target. The selection procedure is based on DNA molecules, each encoding a protein and a structural signal calling for the display of the protein on the outer surface of a bacteriophage. The protein is expressed and the potential binding domain is displayed on the outer surface of the phage. The cells or viruses bearing the binding domains which recognize the target molecule are isolated, by a repetitive selection process called biopanning, and amplified. The successful binding domains are then characterized.

Epitope libraries can also be screened for epitope sequences which mimic the epitope, i.e., sequences which do not identify a continuous linear native sequence that necessarily occurs within a natural protein sequence. These mimicking peptides are called mimotopes. In most cases mimotopes are short peptides which can be readily synthesized in large amounts. Mimotopes of various binding sites have been found. For example, U.S. Pat. No. 5,877,155 provides an isolated peptide that functionally mimics a binding site for a monoclonal antibody, the monoclonal antibody recognizing an epitope within the human platelet glycoprotein Ib/IX complex.

There is an unmet medical need for peptides capable of eliciting or stimulating an anti-tumor immune response in vivo.

SUMMARY OF THE INVENTION

The present invention now provides peptides that are useful as immunomodulatory agents, for example, in stimulating immune responses and in tumor growth inhibition. Thus, these peptides are useful in treatment of cancer and in treatment of autoimmune diseases.

In addition, the invention provides peptides that are recognized by BAT monoclonal antibody and, in particular, peptides that comprise epitopes or mimotopes recognized by the immunomodulatory antibody designated BAT-1.

The invention also relates to a diagnostic agent and method for diagnosing cancer in a subject. These can include an antibody recognizing at least one epitope encompassed within any of the peptides of the invention.

The term 'epitope' referred to herein, relates to that part of an antigenic molecule that is recognized and bound by a T-cell receptor or by a B-cell receptor (i.e. a determinant on a large molecule against which an antibody can be produced and to which it will bind). The term as used herein is intended to include antigenic determinants of naturally occurring molecules or synthetic molecules that can mimic naturally occurring antigenic determinants. Molecules which mimic the naturally occurring antigenic determinants may also be referred to as 'mimotopes', and these terms may be used interchangeably in reference to epitopes which are not formed by a contiguous segment of the primary sequence of an antigen.

The peptides of the invention are recognized by the BAT-1 monoclonal antibody, also denoted herein as BAT, which is disclosed in WO95/20605 and WO00/58363. The peptides of the invention are further recognized by genetically modified antibodies which retain the biological activity of BAT, including chimeras or CDR-grafted antibodies. A chimeric human-mouse BAT antibody, containing mouse variable regions joined to human constant regions, is disclosed in WO00/58363.

It has previously been shown that BAT monoclonal antibody is beneficial in treating a variety of tumors including but not limited to: melanoma, lung carcinoma, prostate cancer, breast cancer, lymphomas and leukemias, colon carcinoma, and fibrosarcomas. The peptides and polynucleotides of the present invention are useful to elicit an immune response that will obviate the necessity to treat an individual with the antibodies themselves. Thus, the peptides and polynucleotides may be used to elicit antibodies that share the attributes of the previously known BAT antibody.

In addition, the peptides of the invention are immunomodulatory. The peptides of the invention may serve as immunostimulatory agents to elicit anti-tumor activity or may serve as agents for immunotherapy or as immune-stimulators against infections, including in immunization procedures. Conversely, they can serve to inhibit undesirable immune responses such as immune responses that are involved in inflammatory conditions, including but not limited to autoimmune diseases. As immunomodulators, these peptides can induce shifts in the immune system from undesirable responses to beneficial responses. Thus, for example the peptides of the invention could be used to induce shifts from T helper 1 (TH1) to T helper 2 (TH2) responses that have been postulated to be of therapeutic value for suppressing or preventing autoimmune diseases or disorders.

There is thus provided, according to one embodiment of the invention, a peptide comprising at least one epitope recognized by a BAT monoclonal antibody, selected from:

```
                                          (SEQ ID NO 1)
Pro Arg Arg Ile Lys Pro Arg Lys Ile Met Leu Gln

                                          (SEQ ID NO 2)
Pro Arg Arg Ile Lys Pro Arg Lys Ile Met Leu
Gln-amide

                                          (SEQ ID NO 3)
Pro Arg Arg Phe Lys Pro Arg Lys Ile Asn/Asp Leu
Gln

                                          (SEQ ID NO 4)
Pro Arg Arg Ile Lys Pro Arg Lys Ile Asn/Asp Phe
Gln

                                          (SEQ ID NO 5)
Pro Arg Arg Ile Lys Pro Arg Lys Ile Asn/Asp Leu
Gln

                                          (SEQ ID NO 6)
Pro Arg Arg Ile Lys Ala Arg Lys Ile Met Leu Gln

                                          (SEQ ID NO 7)
Pro Arg Lys Ile Lys Pro Arg Lys Ile Met Leu Gln

                                          (SEQ ID NO 8)
-   -   Arg Ile Lys Pro Arg Lys Ile Met Leu Gln

                                          (SEQ ID NO 9)
Pro Arg Arg Ile Lys Pro Arg Lys Ile Met -   -

                                         (SEQ ID NO 10)
acetyl-Pro Arg Arg Ile Lys Pro Arg Lys Ile Met Leu
Gln

                                         (SEQ ID NO 11)
Gln Arg Ile Leu Gln Gln Ile Asn Leu Pro Arg Ile

                                         (SEQ ID NO 12)
Gln Arg Ile Leu Gln Gln Ile Asn Leu Ala Arg Ile

                                         (SEQ ID NO 13)
Gln Arg Ile Leu Gln Glu Ile Asn Leu Pro Arg Ile

                                         (SEQ ID NO 14)
Gln Arg Ile Leu Gln Gln Ile Asn Leu Pro Lys Ile

                                         (SEQ ID NO 15)
-   -   Ile Leu Gln Gln Ile Asn Leu Pro Arg Ile

                                         (SEQ ID NO 16)
Gln Arg Ile Leu Gln Gln Ile Asn Leu Pro -   -

                                         (SEQ ID NO 17)
Asn Arg Ile Arg Thr Asn Thr Lys Leu Met Asn Ser
```

According to certain currently preferred embodiments, the present invention provides a peptide comprising at least one epitope recognized by a BAT monoclonal antibody selected from SEQ ID NOs 1, 6, 8, 9, 10, 14 and 16.

According to another particular embodiment, the present invention provides a peptide comprising at least one epitope recognized by a BAT monoclonal antibody, selected from: a peptide, a fragment of a peptide, a homolog, a variant, a derivative or a salt of a peptide having the sequence of any one of SEQ ID NOs 1 through 17, wherein the biological activity of said peptides or fragments is retained.

According to yet another particular embodiment, the present invention provides a combination of any one of the peptides comprising at least one epitope recognized by a BAT monoclonal antibody, selected from: a peptide, a fragment of a peptide, a homolog, a variant, a derivative or a salt of a peptide having the sequence of any one of SEQ ID NOs 1 through 17, wherein the biological activity of said peptides or fragments is retained.

According to certain currently preferred embodiments, the present invention provides a peptide comprising at least one epitope recognized by a BAT monoclonal antibody, selected from: a peptide, a fragment of a peptide, a homolog, a variant, a derivative or a salt of a peptide having the sequence of any one of SEQ ID NOs 1, 6, 8, 9, 10, 14, 16, wherein the biological activity of said peptides or fragments is retained.

According to yet another currently preferred embodiments, the present invention provides a combination of any one of the peptides comprising at least one epitope recognized by a BAT monoclonal antibody, selected from: a peptide, a fragment of a peptide, a homolog, a variant, a derivative or a salt of a peptide having the sequence of any one of SEQ ID NOs 1, 6, 8, 9, 10, 14, 16, wherein the biological activity of said peptides or fragments is retained.

According to yet another particular embodiment, the peptide of the present invention is capable of inhibiting binding of BAT monoclonal antibody to lymphoma cells, for example, to Daudi or Jurkat cells.

Furthermore, in another embodiment, the present invention provides a peptide useful for inhibiting tumor growth, selected from: a peptide, a fragment of a peptide, a homolog, a variant, a derivative or a salt of a peptide having the sequence of any one of SEQ ID NOs 1 through 17, wherein the biological activity of said peptides or fragments is retained.

According to yet another particular embodiment, the present invention provides a combination of any one of the peptides useful for inhibiting tumor growth, selected from: a peptide, a fragment of a peptide, a homolog, a variant, a derivative or a salt of a peptide having the sequence of any one of SEQ ID NOs 1 through 17, wherein the biological activity of said peptides or fragments is retained.

In certain currently preferred embodiments, the present invention provides a peptide useful for inhibiting tumor growth, selected from: a peptide, a fragment of a peptide, a homolog, a variant, a derivative or a salt of a peptide having the sequence of any one of SEQ ID NOs 1, 6, 8, 9, 10, 14, 16, wherein the biological activity of said peptides or fragments is retained.

According to another certain currently preferred embodiments, the present invention provides a combination of any one of the peptides useful for inhibiting tumor growth, selected from: a peptide, a fragment of a peptide, a homolog, a variant, a derivative or a salt of a peptide having the sequence of any one of SEQ ID NOs 1, 6, 8, 9, 10, 14, 16, wherein the biological activity of said peptides or fragments is retained.

In another embodiment, the present invention provides a peptide capable of inducing an immune response against tumor cells, selected from: a peptide, a fragment of a peptide, a homolog, a variant, a derivative or a salt of a peptide having the sequence of any one of SEQ ID NOs 1 through 17, wherein the biological activity of said peptides or fragments is retained.

According to yet another particular embodiment, the present invention provides a combination of any one of the peptides capable of inducing an immune response against tumor cells, selected from: a peptide, a fragment of a peptide, a homolog, a variant, a derivative or a salt of a peptide having the sequence of any one of SEQ ID NOs 1 through 17, wherein the biological activity of said peptides or fragments is retained.

In certain currently preferred embodiments, the present invention provides a peptide capable of inducing an immune response against tumor cells, selected from: a peptide, a fragment of a peptide, a homolog, a variant, a derivative or a salt of a peptide having the sequence of any one of SEQ ID NOs 1, 6, 8, 9, 10, 14, 16, wherein the biological activity of said peptides or fragments is retained.

According to currently preferred embodiments, the present invention provides a combination of any one of the peptides capable of inducing an immune response against tumor cells, selected from: a peptide, a fragment of a peptide, a homolog, a variant, a derivative or a salt of a peptide having the sequence of any one of SEQ ID NOs 1, 6, 8, 9, 10, 14, 16, wherein the biological activity of said peptides or fragments is retained.

Further provided according to another embodiment of the invention, is a polynucleotide encoding at least one peptide recognized by BAT monoclonal antibodies. The nucleic acid sequences include both the DNA sequence that is transcribed into RNA and the RNA sequence that is translated into a peptide.

According to certain embodiments of the present invention, the polynucleotide comprises a sequence selected from the group consisting of:

```
(SEQ ID NO 18) CCTCGACGAATAAAGCCCAGGAAGATCATGCTGCAA
(SEQ ID NO 26) CAGAGGATACTGCAGCAAATTAATCTTCCCAGGATC
(SEQ ID NO 32) AACCGAATCAGGACAAATACTAAGCTCATGAACAGC
```

According to other embodiments, the polynucleotides of the invention are inferred from the amino acid sequence of the peptides of the invention. As is known in the art several alternative polynucleotides are possible due to redundant codons, while retaining the biological activity of the translated peptides.

Thus, according to further embodiments, the polynucleotide of the invention comprise a sequences selected from:

```
(SEQ ID NO 19) CCTCGACGATTYAAGCCCAGGAAGATCRAYCTGCAA
(SEQ ID NO 20) CCTCGACGAATAAAGCCCAGGAAGATCRAYTTYCAA
(SEQ ID NO 21) CCTCGACGAATAAAGCCCAGGAAGATCRAYCTGCAA
(SEQ ID NO 22) CCTCGACGAATAAAGGCXAGGAAGATCATGCTGCAA
(SEQ ID NO 23) CCTCGAAAYATAAAGCCCAGGAAGATCATGCTGCAA
(SEQ ID NO 24) CGAATAAAGCCCAGGAAGATCATGCTGCAA
(SEQ ID NO 25) CCTCGACGAATAAAGCCCAGGAAGATCATG
(SEQ ID NO 27) CAGAGGATACTGCAGCAAATTAATCTTGCXAGGATC
(SEQ ID NO 28) CAGAGGATACTGCAGGARATTAATCTTCCCAGGATC
(SEQ ID NO 29) CAGAGGATACTGCAGCAAATTAATCTTCCCAAYATC
(SEQ ID NO 30) ATACTGCAGCAAATTAATCTTCCCAGGATC
(SEQ ID NO 31) CAGAGGATACTGCAGCAAATTAATCTTCCC
```

wherein Y=T or C; R=A or G; X=T or C or A or G)

The nomenclature used to describe peptide and polynucleotide compounds of the invention follows the conventional practice wherein the amino group (N-terminus) and the 5' are presented to the left and the carboxyl group (C-terminus) and 3' to the right.

It is to be understood explicitly that the scope of the present invention encompasses homologs, analogs, variants, derivatives and salts, including shorter and longer peptides and polynucleotides, as well as peptide and polynucleotide analogs with one or more amino acid or nucleic acid substitution, as well as amino acid or nucleic acid derivatives, non-natural amino or nucleic acids and synthetic amino or nucleic acids as are known in the art, with the stipulation that these modifications must preserve the biological activity of the original molecule. Specifically any active fragments of the active peptides as well as extensions, conjugates and mixtures are disclosed according to the principles of the present invention.

Also provided, according to another embodiment of the invention, is a construct comprising a polynucleotide encoding for at least one peptide recognized by a BAT monoclonal antibody.

Furthermore, in another embodiment, the present invention provides a vector, for example, a plasmid or a virus, comprising a polynucleotide encoding at least one peptide recognized by a BAT monoclonal antibody.

Further provided, according to other embodiment of the invention, is a host cell comprising a polynucleotide encoding at least one peptide recognized by the BAT monoclonal antibody.

In one embodiment the host cell is capable of expressing at least one epitope recognized by BAT monoclonal antibody.

In yet another embodiment, the present invention provides a method and a composition for treating cancer in a subject in need thereof, comprising the step of administering to a patient a therapeutically effective amount of a pharmaceutical composition of the present invention.

In one embodiment the pharmaceutical composition comprises a pharmaceutical carrier and an active ingredient, which is a peptide according to embodiments of the invention.

In another embodiment the pharmaceutical composition comprises a pharmaceutical carrier and an active ingredient, which is a polynucleotide encoding at least one peptide recognized by a BAT monoclonal antibody.

In one embodiment the polynucleotide comprises a sequence selected from SEQ ID NOs 18 through 31.

In currently preferred embodiments the polynucleotide comprises a sequence selected from SEQ ID NOs 18, 22, 24, 25, 29, 31.

Also provided according to an embodiment of the invention is an immunomodulatory vaccine comprising a pharmaceutically acceptable adjuvant, selected from the group of an aluminum salt and an oil emulsion, and at least one peptide recognized by a BAT monoclonal antibody.

In one embodiment, the peptide comprises a sequence selected from SEQ ID NOs 1 to 17.

The term "vaccine" or "vaccination" referred to herein relates to a modality or process that induces modulation of the immune system, for example, but not limited to, a composition or process that induce the activation of T-lymphocytes or that induces the production of antibodies.

According to another embodiment of the invention there is provided a diagnostic agent for detecting the presence of tumor cells comprising a peptide, a fragment of a peptide, a homolog, a variant, a derivative or a salt of a peptide having the sequence of any one of SEQ ID NOs 1 through 17, wherein the biological activity of said peptides or fragments is retained.

According to yet another particular embodiment, the present invention provides a diagnostic agent for detecting the presence of tumor cells comprising a combination of any one of the peptides, a fragment of a peptide, a homolog, a variant, a derivative or a salt of a peptide having the sequence of any one of SEQ ID NOs 1 through 17, wherein the biological activity of said peptides or fragments is retained.

In certain currently preferred embodiments, the peptide comprises the sequence of any one of SEQ ID NOs 1, 6, 8, 9, 10, 14, and 16.

Furthermore, in another embodiment the present invention provides a method for diagnosing cancer comprising the steps of: contacting a sample from a subject with a peptide recognized by a BAT monoclonal antibody; determining the extent of binding of said peptide to the sample; and comparing the extent of binding of said peptide to the sample with a known control (such as a predetermined calibration scale) thereby obtaining information regarding the occurrence of cancer in the sample.

Furthermore, in another embodiment the present invention provides a method for diagnosing an inflammatory disorder or autoimmune disease comprising the steps of: obtaining a sample of immune cells from an individual; exposing said immune cells to at least one peptide recognized by a BAT monoclonal antibody; and monitoring the response of said immune cells compared to the response of said immune cells not exposed to the peptide.

According to another embodiment, the present invention provides an antibody recognizing at least one epitope selected from: a peptide, a fragment of a peptide, a homolog, a variant, a derivative or a salt of a peptide having the sequence of any one of SEQ ID NOs 1 through 17, wherein the biological activity of said peptides or fragments is retained.

According to currently preferred embodiments, the present invention provides an antibody a combination of any one of the peptides comprising at least one epitope recognized by a BAT monoclonal antibody, selected from: a peptide, a fragment of a peptide, a homolog, a variant, a derivative or a salt of a peptide having the sequence of any one of SEQ ID NOs 1 through 17, wherein the biological activity of said peptides or fragments is retained.

Other objects, features and advantages of the present invention will become apparent from the following detailed description and appended claims.

DETAILED DESCRIPTION OF THE PREFERRED EMBODIMENTS

Figure 1:
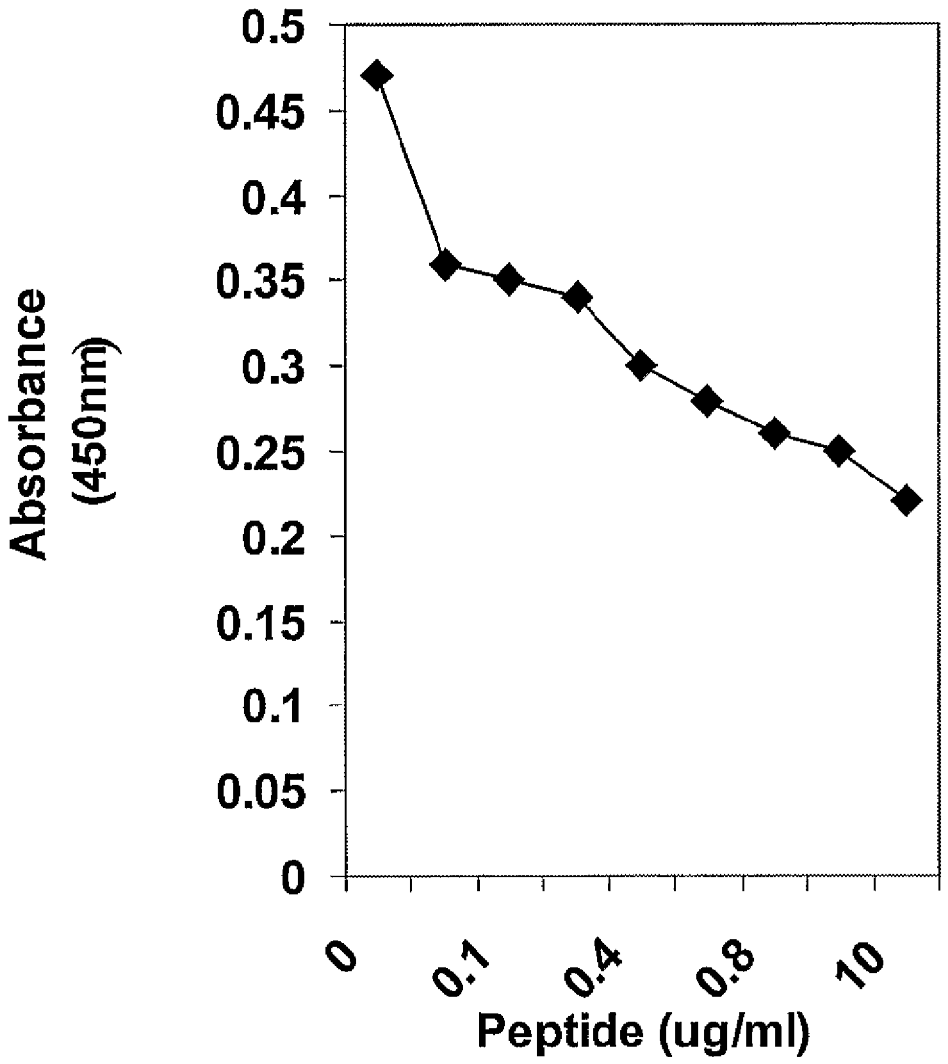
FIG. 1 shows the inhibition of BAT monoclonal antibody binding to immobilized phage bearing the insert of SEQ ID NO 1 (Peptide A) by the free peptide.

The present invention concerns peptides, polynucleotides and pharmaceutical and vaccine compositions including same which are useful in modulation of immune responses, in inhibition of tumor growth, both primary tumor and metastases, in treatment of cancer and of inflammatory disorders including autoimmune diseases by way of prevention and cure. Specifically, the present invention provides vaccines which include peptides recognized by the immune modulator BAT monoclonal antibody which is disclosed in the above-mentioned International Patent Applications WO 95/20605 and WO 00/58363.

a. Preferred Modes for Carrying Out the Invention

According to a first aspect of the present invention there are provided peptides recognized by BAT monoclonal antibody. Several methods for identifying peptides that are capable of binding to the BAT antibody are known in the art. For example, raising peptides against the BAT antibody whereas the peptides may be selected from peptide libraries, such as, bacteriophage library, chemical library, hybridoma cell library; cells preferably B lymphocytes and T cell and more preferably Daudi cells and Jurkat cells; chemical syntheses that might produce a set or a subset of molecules having high affinity for the sequence of BAT monoclonal antibody; designing molecules intended to have a high affinity for BAT sequences using computer-assisted or other theoretical approaches; using in-vitro evolution of nucleic acids capable of binding to the sequence of BAT.

According to preferred embodiments of the present invention a phage epitope library is employed in order to identify peptides that bind BAT monoclonal antibody and to prepare an immunotherapy modality. Most preferably, a 12-mer-phage peptide library constructed using phage M13 is used to identify peptides as the putative antibody binding epitope and consequently to identify the polynucleotide sequence encoding the peptides.

Although the peptide will preferably be substantially free of other naturally occurring host cell proteins or protein fragments, in some embodiments the peptides can be synthetically conjugated to native fragments or particles.

According to a certain preferred embodiments, the 12-mer peptides of the present invention are:

SEQ ID NO 1, also termed hereinafter Peptide A: Pro Arg Arg Ile Lys Pro Arg Lys Ile Met Leu Gln SEQ ID NO 11, also termed hereinafter Peptide B: Gln Arg Ile Leu Gln Gln Ile Asn Leu Pro Arg Ile SEQ ID NO 17, also termed hereinafter Peptide C: Asn Arg Ile Arg Thr Asn Thr Lys Leu Met Asn Ser According to the principles of the present invention the scope of the invention further includes any variants, derivative or salts of the above peptides.

The term "variant" as used herein refers to a peptide sequence that possesses at least one modified structural property compared to the original peptide while substantially retaining the biological activity of the resulting peptide as compared with the original peptide or the BAT monoclonal antibody. For example, one or more of the amino acid residues of the original peptides are replaced by different amino acid residues, or are deleted, or one or more amino acid residues are added to the original peptides, a peptide bond is modified, cyclization is introduced to the structure of the original peptide, a backbone is modified. A variant may have altered binding to BAT monoclonal antibody than the original peptide. A variant may have at least 70% identity with the original peptide, preferably 80% or 90% identity. A variant may also be referred to as 'analog' or 'homolog', and these terms may be used interchangeably.

In one embodiment, the present invention comprises a salt of peptide of the invention. The term "salt" includes acid addition salts which are formed with inorganic acids such as, for example, hydrochloric or phosphoric acids, or such organic acids as acetic, oxalic, tartaric, mandelic, and the like. The term also includes base addition salts which are formed from inorganic bases such as, for example, sodium, potassium, ammonium, and calcium, and from organic bases such as isopropylamine, trimethylamine, histidine, and the like.

In another embodiment the present invention comprises a derivative of a peptide of the invention. The term "derivative" of a peptide as used herein refers to a peptide that contains additional chemical moieties not normally a part of the peptide. Such modifications may be introduced into the molecule by reacting targeted amino acid residues of the peptide with an organic derivatizing agent that is capable of reacting with selected side chains or terminal residues. Examples of chemical derivatives, by way of illustration and not by way of limitation, include a peptide in which the C-terminus or the N-terminus of the peptides of the present invention, or both, are substituted with a carboxylic acid protecting group or an amine protecting group, respectively. Suitable protecting groups are described in Green and Wuts, "Protecting Groups in organic Synthesis", John Wiley and Sons, Chapters 5 and 7, 1991. Examples of N-terminal protecting groups include acyl groups ($—CO—R_1$) and alkoxy carbonyl or aryloxy carbonyl groups ($—CO—O—R_1$), wherein $R_1$ is an aliphatic, substituted aliphatic, benzyl, substituted benzyl, aromatic or a substituted aromatic group. Examples of acyl groups include acetyl, (ethyl)-CO—, n-propyl-CO—, iso-propyl-CO—, n-butyl-CO—, sec-butyl-CO—, t-butyl-CO— and phenyl-CO—. Examples of alkoxy carbonyl and aryloxy carbonyl groups include $CH_3—O—CO—$, (ethyl)-O—CO—, n-propyl-O—CO—, iso-propyl-O—CO—, n-butyl-O—CO—, sec-butyl-O—CO—, t-butyl-O—CO—, phenyl-O—CO—. The carboxyl group at the C-terminus can be protected, for example, as an amide (i.e., the hydroxyl group at the C-terminus is replaced with $—NH_2$, $—NHR_2$ and $—NR_2R_3$) or ester (i.e. the hydroxyl group at the C-terminus is replace with $—OR_2$). $R_2$ and $R_3$ are independently an aliphatic, substituted aliphatic, benzyl, substituted benzyl, aryl or a substituted aryl group.

A variant, derivative or salt of a peptide of the invention may be advantageous, as compared to the original peptide, if they possess at least one of the following properties: improved solubility, prolonged duration of action, superior biological activity, increased stability to degradation by enzymes and therefore increased in vivo half lives, eliminated or attenuated undesirable side effects and the like.

The term "biological activity" as used herein, includes at least one of the following activities: induction of anti-tumor effect, modification of immune response, stimulation of immune response against tumor cells, inhibition of the binding of BAT monoclonal antibody to lymphoma cells—particularly Daudi or Jurkat cells, detection of cancer, detection of an inflammatory disorder or autoimmune disease or, prevention of tumor development.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, and antibodies of the invention in prevention of the occurrence of tumor in the first place.

The peptide or variant may be generated through recombinant DNA technologies, well known to those skilled in the art, following cloning into an expression vector, transfection into host cells and the protein harvesting according to methods known in the art. In a preferred embodiment the peptides and variants are prepared by known peptide synthesis techniques.

Currently preferred embodiments of the invention are variants obtained by conservative modifications introduced to SEQ ID NO 1 (Peptide A). Currently most preferred embodiments include the following variants:

```
                                            (SEQ ID NO 2)
Pro Arg Arg Ile Lys Pro Arg Lys Ile Met Leu
Gln-amide

                                            (SEQ ID NO 3)
Pro Arg Arg Phe Lys Pro Arg Lys Ile Asn/Asp Leu
Gln

                                            (SEQ ID NO 4)
Pro Arg Arg Ile Lys Pro Arg Lys Ile Asn/Asp Phe
Gln

                                            (SEQ ID NO 5)
Pro Arg Arg Ile Lys Pro Arg Lys Ile Asn/Asp Leu
Gln

                                            (SEQ ID NO 6)
Pro Arg Arg Ile Lys Ala Arg Lys Ile Met Leu Gln

                                            (SEQ ID NO 7)
Pro Arg Lys Ile Lys Pro Arg Lys Ile Met Leu Gln

                                            (SEQ ID NO 8)
-   -   Arg Ile Lys Pro Arg Lys Ile Met Leu Gln

                                            (SEQ ID NO 9)
Pro Arg Arg Ile Lys Pro Arg Lys Ile Met -   -

                                           (SEQ ID NO 10)
acetyl-Pro Arg Arg Ile Lys Pro Arg Lys Ile Met Leu
Gln
```

Additional currently preferred embodiments of the invention are variants obtained by conservative modifications introduced to SEQ ID NO 11 (Peptide B). Currently most preferred embodiments include the following variants:

```
                                           (SEQ ID NO 12)
Gln Arg Ile Leu Gln Gln Ile Asn Leu Ala Arg Ile

                                           (SEQ ID NO 13)
Gln Arg Ile Leu Gln Glu Ile Asn Leu Pro Arg Ile

                                           (SEQ ID NO 14)
Gln Arg Ile Leu Gln Gln Ile Asn Leu Pro Lys Ile

                                           (SEQ ID NO 15)
-   -   Ile Leu Gln Gln Ile Asn Leu Pro Arg Ile

                                           (SEQ ID NO 16)
Gln Arg Ile Leu Gln Gln Ile Asn Leu Pro -   -
```

The biological activity of the variants is monitored and compared with that of the selected peptides and of the BAT monoclonal antibody as exemplified hereinbelow.

Without wishing to be bound by any theory, it is possible that the peptides of the invention elicit an immune response similar to that obtained by the BAT monoclonal antibody.

Thus, preferred methods for monitoring the biological activity of the peptides and the variants include: competitive inhibition with BAT monoclonal antibody to determinants recognized by BAT, e.g. Daudi cells and Jurkat cells; competitive inhibition to determinants recognized by BAT, e.g. Daudi cells and Jurkat cells, between sera of immunized subjects and BAT monoclonal antibody; immunizing with the peptides tumor-bearing animals and monitoring tumor growth; immunizing with the peptides naive animals and monitoring tumor development upon induction of cancer; monitoring immune response upon immunization, preferably monitoring the cytolytic activity of NK and CTL cells upon immunization with the peptides; monitoring lymphocyte proliferation upon immunization with anti-peptides antibodies.

According to a second aspect of the present invention there is provided a construct comprising a polynucleotide encoding for the peptides recognized by the BAT monoclonal antibody.

In several preferred embodiments the polynucleotides of the invention are isolated from the phage clones expressing peptides recognized by BAT monoclonal antibody, and are selected from: SEQ ID NO 18, encoding the peptide of SEQ ID NOS 1 (Peptide A), 2 and 10; SEQ ID NO 26 encoding the peptide of SEQ ID NO 11 (Peptide B); SEQ ID NO 32 encoding the peptide of SEQ ID NO 17 (Peptide C).

According to other general embodiments, the polynucleotides of the invention are derived from the amino acid sequence of the peptides of the invention, including variations due to redundant codons providing that the biological activity of the translated peptide is retained.

Thus, according to further embodiments the polynucleotide of the invention are selected from the group of sequences consisting of:

SEQ ID NO 19 encoding the peptide of SEQ ID NO 3;
SEQ ID NO 20 encoding the peptide of SEQ ID NO 4;
SEQ ID NO 21 encoding the peptide of SEQ ID NO 5;
SEQ ID NO 22 encoding the peptide of SEQ ID NO 6;
SEQ ID NO 23 encoding the peptide of SEQ ID NO 7;
SEQ ID NO 24 encoding the peptide of SEQ ID NO 8;
SEQ ID NO 25 encoding the peptide of SEQ ID NO 9;
SEQ ID NO 26 encoding the peptide of SEQ ID NO 10;
SEQ ID NO 27 encoding the peptide of SEQ ID NO 12;
SEQ ID NO 28 encoding the peptide of SEQ ID NO 13;
SEQ ID NO 29 encoding the peptide of SEQ ID NO 14;
SEQ ID NO 30 encoding the peptide of SEQ ID NO 15;
SEQ ID NO 31 encoding the peptide of SEQ ID NO 16;

The constructs comprising the polynucleotides encoding the peptides of the invention may further include promoters, enhancers and other regulatory sequences necessary for expression, transcription and translation, as are well known in the art. The constructs can be further provided with appropriate linkers and can be ligated into expression vectors available in the art. The vectors can be used to transform suitable hosts to produce the desired peptides. Vectors may include restriction enzyme sites for the insertion of additional genes and for selection markers, as well as elements necessary for propagation and maintenance of vectors within cells.

Cells presenting peptides recognized by the monoclonal antibody BAT are also included in the present invention, for instance, antigen presenting cells including dendritic cells or macrophages which are also known as useful immunogens.

An antibody recognizing an epitope within any one of SEQ ID NOs 1 through 17 is further provided in the present invention.

The term "antibody" is used herein in the broadest sense and covers monoclonal antibodies (including full length monoclonal antibodies) and antibody fragments so long as they exhibit the desired biological activity. "Antibody fragments" comprise a portion of a full length antibody, generally the antigen binding or variable region thereof. Examples of antibody fragments include Fab, Fab', $F(ab')_2$, and Fv fragments; diabodies; linear antibodies; single-chain antibody molecules; and multispecific antibodies formed from antibody fragments.

Methods for the production of antibodies are well known in the arts, including eliciting antibodies from the sera of subjects immunized with the target determinant of said antibodies, as well as recombinant techniques.

b. Pharmacology

The present invention further relates to a pharmaceutical composition which includes at least one epitope recognized by the BAT monoclonal antibody as the pharmaceutically active ingredient. The pharmaceutically active ingredient is selected from the group containing: a peptide comprising at least one epitope, a polynucleotide encoding at least one epitope, a polynucleotide encoding at least one of said peptide, a construct comprising at least one of said polynucleotide, a vector comprising at least one of said construct.

The peptide of the present invention, or a pharmacologically acceptable salt thereof may be mixed with an excipient, carrier, diluent, and optionally, a preservative or the like, pharmacologically acceptable vehicles as known in the art. Examples of excipients include, glucose, mannitol, inositol, sucrose, lactose, fructose, starch, cornstarch, microcrystalline cellulose, hydroxypropylcellulose, hydroxypropyl-methylcellulose, polyvinylpyrrolidone and the like. Optionally, a thickener may be added, such as a natural gum, a cellulose derivative, an acrylic or vinyl polymer, or the like. The pharmaceutical composition including the peptide may further comprise a biodegradable polymer selected from poly-1,4-butylene succinate, poly-2,3-butylene succinate, poly-1,4-butylene fumarate and poly-2,3-butylene succinate, incorporating the peptide of the invention as the pamoate, tannate, stearate or palmitate thereof. Such compositions are known in the art as described, for example, in U.S. Pat. No. 5,439,688.

The pharmaceutically active ingredient of the composition may be conjugated to a matrix or to a proteinaceous carrier, for example tetanus or diphtheria toxoids or oxidized KLH, in order to stimulate T cell help, or to other immuno-potentiating agents as well as biological response modifiers such as interferons, interleukins etc., in order to stimulate the immune system. The compositions for administration to humans may further comprise adjuvants that are suitable for human use, such as alum, which is approved for human use, or submicron emulsions that are intended for human use as disclosed for example in WO95/11700. Appropriate ranges of ingredients for preparing compositions with or without additional diluents, carriers or adjuvants are known in the art.

The preparation of pharmaceutical compositions comprising peptides is well known in the art, as disclosed for example in U.S. Pat. Nos. 5,736,519, 5,733,877, 5,418,219, 5,354,900, 5,298,246, 5,164,372, 4,900,549 and 4,457,917. Means for processing the pharmaceutical compositions of the present invention include, without limitations, conventional mixing, dissolving, granulating, grinding, pulverizing, dragee-making, levigating, emulsifying, encapsulating, entrapping or lyophilizing processes.

According to yet another aspect of the present invention a peptide vaccine is provided. The two major types of peptide vaccine are: peptides mixed with adjuvant substances and peptides which are introduced together with an antigen presenting cell (APC; Mayordomo et al., Nature Med. 1:1297, 1995). The most common cells used for the latter type of vaccine bone marrow and peripheral blood derived dendritic cells, as this cells express costimulatory molecules that help activation of CTL. WO00/06723 discloses a cellular vaccine composition which includes an antigen presenting cell presenting tumor associated antigen peptides. Presenting the peptide can be effected by loading the APC with a polynucleotide (e.g., DNA, RNA) encoding the peptide or loading the APC with the peptide itself.

In accordance with the first type of peptide vaccine, adjuvant substances that stimulate immunogenicity are mixed with the peptide in order to improve the immune response to the peptide. Immunological adjuvants have generally been divided into two basic types: aluminum salts and oil emulsions. Aluminum phosphate and hydroxide (alum) adjuvants induce elevated levels of antibody against antigens in alum-based vaccines above those obtained with the corresponding aqueous vaccine. Numerous alum-based vaccines, including methods of preparation thereof, were developed as, for example, disclosed in U.S. Pat. Nos. 5,747,653, 6,013,264, 6,306,404 and 6,372,223. However, aluminum compounds have not always enhanced the immunogenicity of vaccines.

The main components of the oil-based adjuvants are: oil, emulsifier and immunostimulant. The earliest types of emulsified oil-based adjuvants are Incomplete Freund's Adjuvant (IFA), consisting of an approximately 50:50 water-in-oil emulsion, and complete Freund's adjuvant (CFA), a similar preparation with inclusion of killed mycobacteria. The powerful antibody-stimulating effect of CFA has not been surpassed by any other adjuvant. However, because of severe toxic reactions CFA can be used only for experimental purposes and not in human or veterinary vaccines. The use of IFA in humans has been limited to those clinical situations in which aqueous vaccines are relatively impotent and aluminum compounds have not provided enough adjuvant activity. Example of improved emulsions as vaccine adjuvants, by enhancing the immunogenicity of the antigen, include submicron emulsions as disclosed in U.S. Pat. No. 5,961,970 and solid fat nanoemulsions as disclosed in U.S. Pat. No. 5,716,637 for example.

Preferred means for administering peptides are through intravenous, intramuscular or subcutaneous administration. Oral administration is expected to be less effective, because a peptide may be digested before being taken up. Decomposition in the digestive tract may be lessened by use of certain compositions, for instance, by confining the peptide of the invention in microcapsules such as liposomes. The pharmaceutical composition of the invention may also be administered to other mucous membranes. The pharmaceutical composition is then provided in the form of a suppository, nasal spray or sublingual tablet.

The uptake of a peptide of the invention may be facilitated by a number of methods. For instance, a non-toxic derivative of the cholera toxin B subunit, or of the structurally related subunit B of the heal-labile enterotoxin of enterotoxic *Eschericia coli* may be added to the composition, as disclosed in U.S. Pat. No. 5,554,378.

The peptides according to an embodiment of the invention may be also administered via liposomes, slow releasing particles and the like, as known in the art, so as to increase the immunogenicity of the peptides.

A composition according to an embodiment of the invention can be directly administered to an individual for immunizing the individual. Alternatively, in accordance with an embodiment of the invention, the peptides may be used to generate new antibodies with the attribute and activities of known BAT monoclonal antibodies. Ex-vivo activation of T-cells by these peptides may also elicit the desired activity of immunostimulation. Thus, the composition can be used for inducing antibodies in an ex-vivo system and the induced antibodies can then be administered to an individual for treating an autoimmune disease, an infection or cancer. The composition can also be used in an ex-vivo system to stimulate T-cells to be administered in a process of adoptive immunotherapy, as described in the art.

The present invention also includes the use of the peptide or polynucleotide as a diagnostic agent for diagnosing cancer in an individual. According to an embodiment of the invention a sample from a individual, such as a blood sample or a sample from a patient's GI tract fluids, or cerebrospinal fluid or any other relevant sample can be contacted, in vivo or in vitro, with a peptide or polynucleotide according to the invention and the extent of binding of the peptide or polynucleotide to the sample can be determined, such as by ELISA, so as to provide information regarding the occurrence of BAT in the sample. For example antibodies to the peptides of the invention may be used to diagnose cancer or to monitor its progression if present in a body fluid especially serum or plasma. Conversely, in the patient's lymph nodes especially in draining lymph nodes in proximity to a suspected tumor, it may be possible to screen the T cells using the peptides of the invention.

The present invention provides methods for the treatment of autoimmune diseases, cancer and for anti-cancer vaccination. Pharmaceutical compositions suitable for use in context of the present invention include compositions wherein the active ingredients are contained in an amount effective to achieve the intended purpose. All formulations for administration should be in dosages suitable for the chosen route of administration. More specifically, a "therapeutically effective" dose means an amount of a compound effective to prevent, alleviate or ameliorate symptoms of a disease of the subject being treated. Determination of a therapeutically effective amount is well within the capability of those skilled in the art, especially in light of the detailed disclosure provided herein.

Toxicity and therapeutic efficacy of the compositions described herein can be determined by standard pharmaceutical procedures in cell cultures or experimental animals, e.g., by determining the $IC_{50}$ (the concentration which provides 50% inhibition) and the maximal tolerated dose for a subject compound. The data obtained from these cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. Depending on the severity and responsiveness of the condition to be treated, dosing can also be a single administration of a slow release composition, with course of treatment lasting from several days to several weeks or until cure is effected or diminution of the disease state is achieved. The amount of a composition to be administered will, of course, be dependent on the subject being treated, the severity of the affliction, the manner of administration, the judgment of the prescribing physician, and all other relevant factors.

EXAMPLES

The present invention will be further described and exemplified by the following non-limitative examples.

Example 1

Preparation of BAT Monoclonal Antibody

BAT was generated, purified and characterized as previously disclosed in WO 95/20605, WO 00/58363 and subsequent publications. In brief, BALB-C mice were immunized with membranes of Daudi cells. Spleen cells were fused with myeloma NSO cells. Clones producing BAT were selected by the ability of supernatants to bind Daudi cells and to induce proliferation of peripheral blood mononuclear cells. Hybridoma cells were grown in RPMI 1640 supplemented with 10% fetal calf serum (for Experiment 1 in Example 2) or with PFHM serum free protein media (GIBCO; for Experiment 2 in Example 2), sodium pyruvate, glutamine, and antibiotics and incubated at 37° C. in a humidified atmosphere containing 5% $CO_2$. BAT was purified on a protein G Sepharose column according to manufacturer's instructions (Pharmacia Corp. NJ, USA). Biotinylation, was performed as follows: 100 μg of the immunoglobulin fraction of BAT monoclonal antibody in 1 ml of 0.1 M NaHCO3, pH 8.6, was incubated for 2 hours at room temperature with 5 μg of biotin amidocoproate N-hydroxysuccinimide ester (SIGMA, Israel) from a stock solution of 1 mg/ml in dimethylformamide and dialyzed at 4° C. against phosphate buffered saline pH 7.4.

Example 2

Isolation of Peptides by Phage-Display Analysis

Experiment 1

Materials and Methods a. Isolation of Epitope-Presenting Phage from a Phage Epitope Library The phage display peptide library was based on a combinatorial library of random 12-mer peptides fused to a minor coat protein (pIII) of M13 phage. A library sample containing $4\times10^{10}$ infectious phage particles was subjected to 6 rounds of panning and amplification. For each selection cycle 100 μg of biotinylated BAT monoclonal antibody was used. The phage was pre-incubated with the biotinylated antibody at room temperature for 1 hour. The reaction mixtures were then layered in 1 ml of TBS 0.5% Tween on streptavidin coated and blocked 60-mm polystyrene Petri dishes for 30 minutes at room temperature. Unbound phages were removed by 10 times washings in TBS 0.5% Tween. The remaining phages were eluted with 1 ml 0.2M Glycine-HCl (pH 2.2), 1 mg/ml BSA. The eluate was neutralized and used to infect *E. coli* stain ER2537. After each round of panning phage was titer on LB/IPTG/Xgal plates. The unamplified last round was titered and plaques were used for sequencing.

b. Phage-ELISA

Wells of microtiter plates were coated with 100 μl of a 1:1000 dilution (0.1M NaHCO3, pH 8.6) of rabbit anti-phage M13 serum by incubation overnight at 4° C. Coated plates were washed 3 times with PBS 0.05% Tween 20 and 100 μl of enriched phage clones, containing $10^9$ phage particles, were then added to the wells and incubated for 1 hour at 37° C. Wells were blocked with 1% BSA in PBS for 1 hour at room temperature, washed and incubated with the antibody overnight at 4° C. For inhibition experiments, peptides were preincubated with the antibody for 30 minutes, before their addition to phage coated wells. After washing, bound antibody was detected by incubation with anti-mouse IgG Peroxidase conjugated (Fab specific) for 45 minutes. After washing with o-phenylene diamine (OPD), substrate was added and the color developed was determined by an ELISA reader at 450 nm.

c. FACS Analysis of Peptide-Inhibition Experiments

BAT mAb biotinylated (20 μg/ml) was incubated with different concentrations of the peptide selected from the phage display analysis (0.01-40 μg/ml) overnight at 4° C. Daudi cells ($0.5\times10^6$) were incubated with the antibody or either with the combination of antibody and peptide for 2 hours on ice. After washing streptavidin FITC was added for 30 minutes. Cells were analyzed by a FACScan (Becton Dickinson & Co., NJ, USA).

d. In Vivo Effect of the Peptide Selected from the Phage Display Analysis

C57BL mice were injected with 20 μg of peptide in CFA (complete Freund's adjuvant) into the footpad. Control mice were injected with CFA alone. After seven days a boost was given with 20 μg of the peptide in PBS. B16 melanoma cells ($0.5\times10^6$ cells/mouse) were inoculated, subcutaneous (s.c.), on day 1 or on day 8 after peptide injection and volume of tumor was measured every two days. Blood was taken from mice on day 14, 21 and 28 after peptide injection for testing specific anti-peptide antibody in sera using ELISA method.

Results a. Isolation of Peptide A (SEQ ID NO 1)

Increased enrichment in the number of plaque forming units (pfu) of phages which were positive for binding to BAT mAb was observed after each panning. Following the $4^{th}$ panning pfu was $2\times10^4$ and after the $6^{th}$ panning a number of $1.5\times10^5$ pfu was observed. The number of phages used in each panning was $1\times10^9$. After the sixth panning, 100% of the phages were positive for binding to BAT mAb. DNA from 40 positive clones was sequenced. The 40 phage clones exhibited the amino acid sequence:

(Peptide A, SEQ ID NO 1) PRRIKPRKIMLQ and the nucleic acid sequence:

(SEQ ID NO 18) CCTCGACGAATAAAGCCCAGGAAGATCATGCTGCAA. Binding of the phage was highly specific. Moreover, binding to control antibodies including nonrelated antibody like IgG-3 mAb was not observed.

b. Inhibition of BAT binding to the Selected Phages by the Synthetic Peptide

To ensure that the interaction between the selected phages and BAT mAb is caused by the insert sequences, peptides encompassing this region were synthesized (i.e. Peptide A) and their ability to compete with BAT mAb binding to the phage was assessed. Immobilized phage on microtiter ELISA plates coated with rabbit anti-phage M13 serum was incubated with 6 μg/ml of the antibody. BAT mAb was pre-incubated with increasing amount of synthetic Peptide A. Peptide A inhibited the binding of the antibody in a dose dependent manner with an inhibition concentration ($IC_{50}$) value of $6.6\times10^{-7}$ M (FIG. 1).

c. FACS Analysis of Peptide Inhibition Experiments

Figure 2:
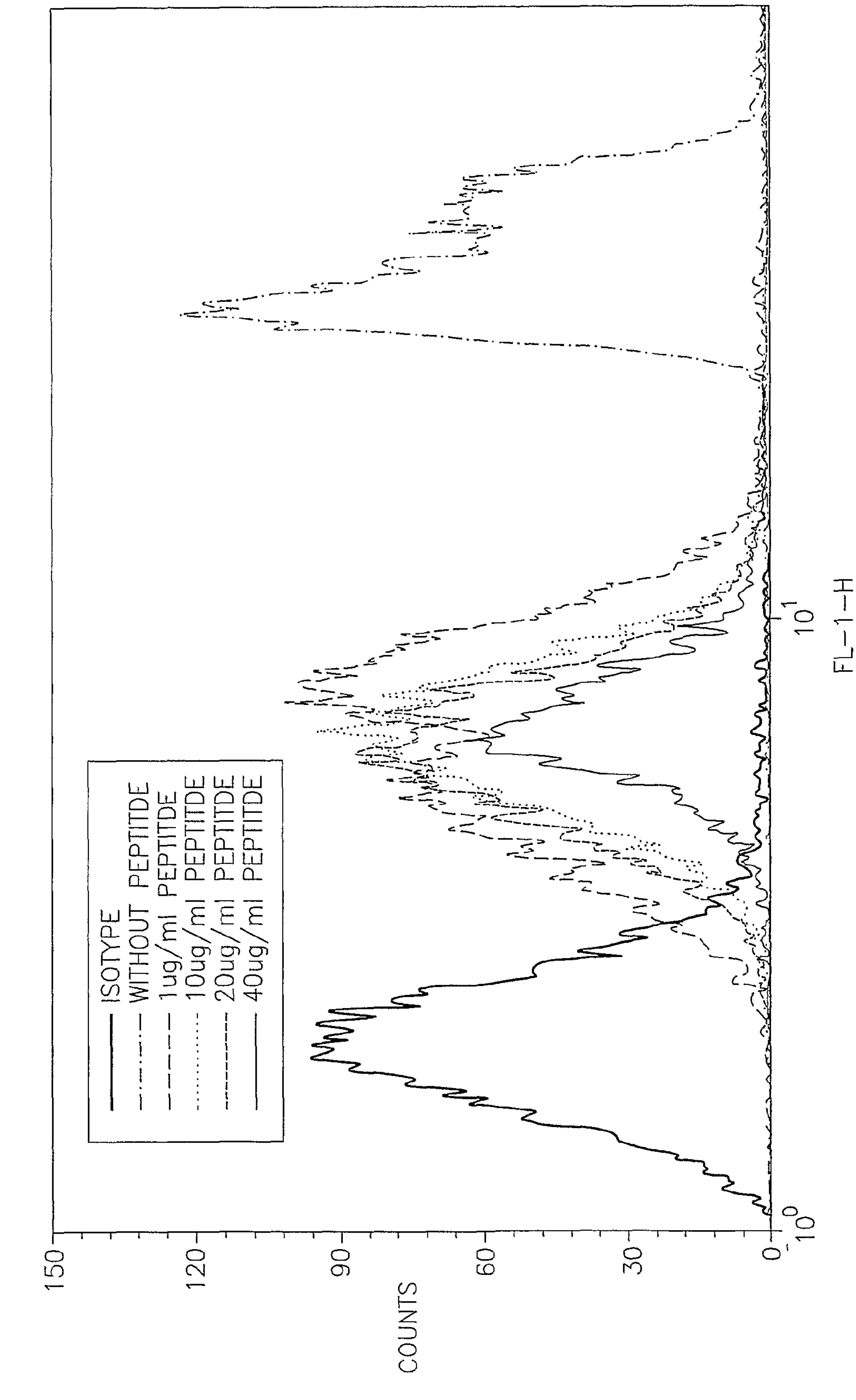
FIG. 2 shows the results of a flow cytometry experiment in which Peptide A inhibition of BAT mAb binding to B-lymphoblastoid cells was determined.

BAT mAb were shown to bind a membrane determinant on Daudi cells. Accordingly, the ability of the synthetic Peptide A to inhibit this binding was assessed. Biotinylated BAT (20 μg/ml) was pre-incubated with increased amounts of Peptide A. The mixture was added to Daudi cells and antibody bound was stained with strept-avidin FITC. Peptide A (1 to 40 μg/ml) inhibited the binding of BAT mAb to Daudi cells in a dose dependent manner (FIG. 2).

d. In Vivo Anti-Tumor Effect of the Selected Peptides.

Figure 3:
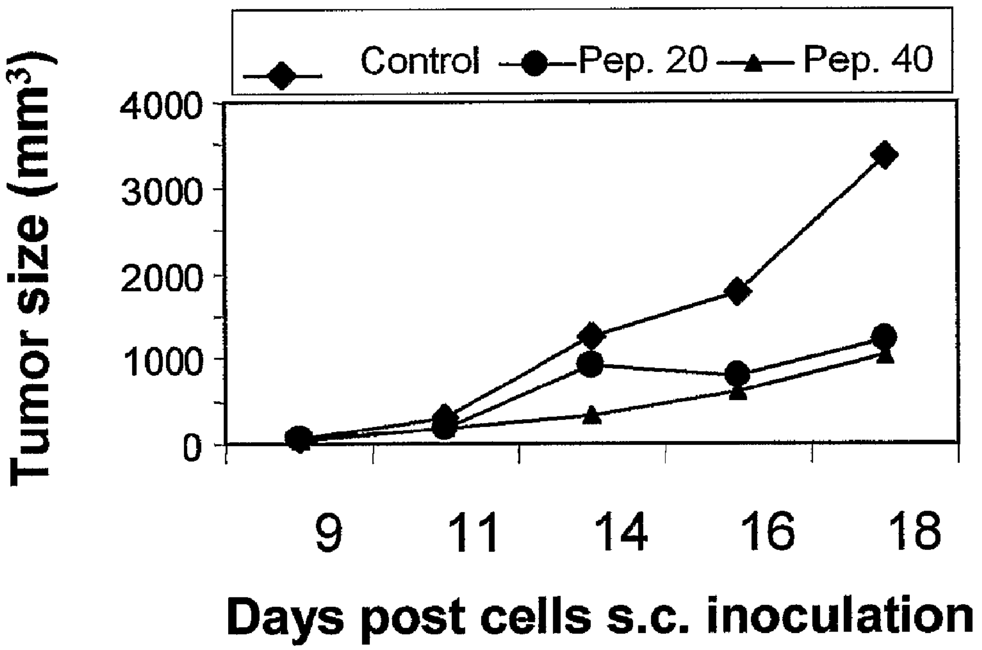
FIG. 3 is a graph showing growth inhibition of melanoma s.c. tumord, by immunization with the synthetic Peptide A.

C57BL mice (n=4), inoculated s.c. with B16 melanoma cells, were immunized with 20 μg of the peptides. Control animals were injected only with CFA. The average melanoma tumor volume was found to decrease in mice immunized with the peptides (FIG. 3).

Figure 4:
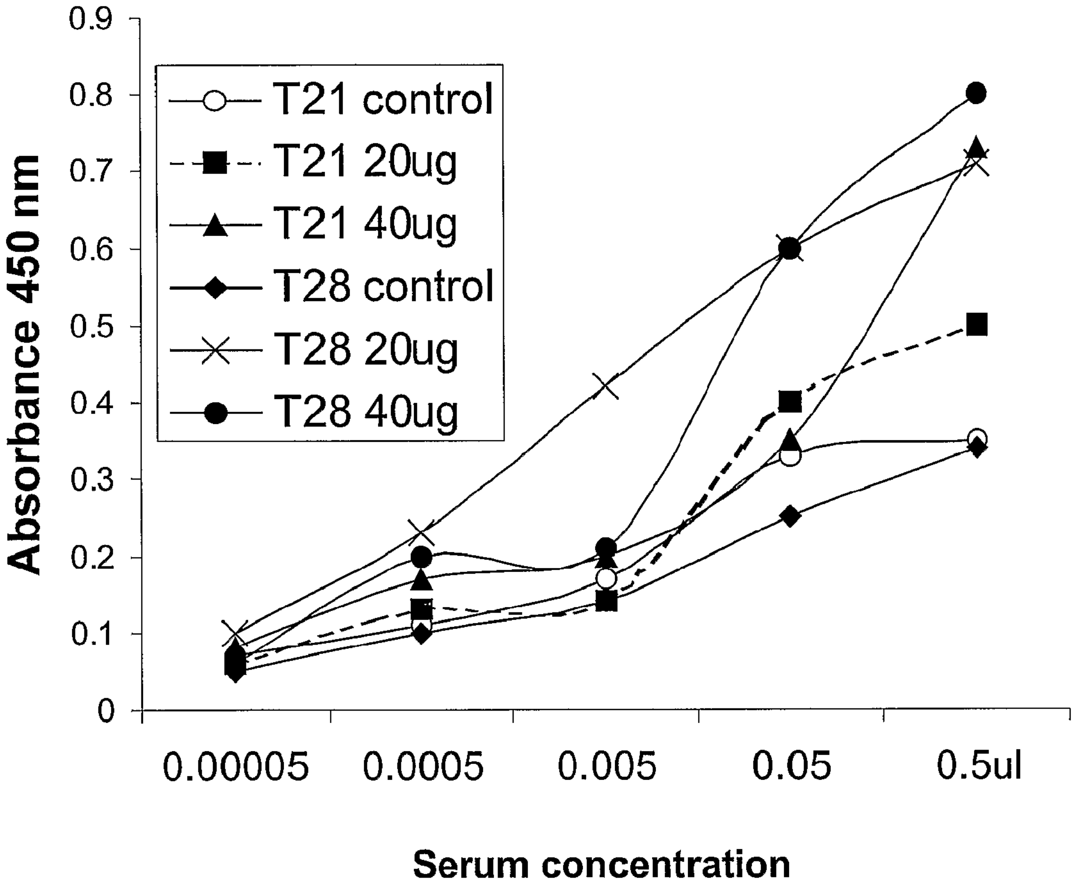
FIG. 4 is a graph showing binding of sera from Peptide A immunized mice to Peptide A coated plates.

Blood samples were withdrawn from control and immunized mice on day 21 and 28 after immunization. Sera from 4 control mice and 4 immunized mice were incubated on microtiter ELISA plates with immobilized peptide. ELISA results indicated that higher concentrations of anti-Peptide A antibodies were observed in the sera of the immunized mice as compared with the sera of control mice (FIG. 4). These results explain the tumor growth inhibition in the treated mice (see FIG. 3).

Experiment 2

Materials and Methods a. Isolation of Epitope-Presenting Phage from a Phage Epitope Library The phage display peptide library is based on a combinatorial library of random peptide 12-mer fused to a minor coat protein (pIII) of M13 phage. A library sample containing $2\times10^{10}$ infectious phage particles was subjected to 3 rounds of panning. For biopanning selection cycles, 20 μg of biotinylated BAT monoclonal antibody was used. The phage was pre-incubated with the biotinylated antibody at room temperature for 1 hour. The reaction mixture was then layered in 1 ml of TBS 0.5% Tween on strept-avidin coated and blocked 60-mm polystyrene Petri dishes for 30 minutes at room temperature. Unbound phages were removed by 10 times washings in TBS 0.5% tween. The remaining phages were eluted with 1 ml 0.2M Glycine-HCl (pH 2.2), 1 mg/ml BSA. The eluate was neutralized and used to infect *E. coli* strain ER2537. After each round of panning phage was titer on LB/IPTG/Xgal plates. After the second cycle of biopanning, the number of phages was amplified. The an-amplified last round was tittered and plaques were used for DNA sequencing.

b. Phage-ELISA

Wells of microtiter plates were coated with 100 μl of a 1:1000 dilution (0.1M NaHCO3, pH 8.6) of rabbit anti-phage M13 serum by incubation overnight at 4° C. Coated plates were washed 3 times with PBS 0.05% Tween. Then, 100 μl of enriched phage clones, containing $10^9$ phage particles, were then added to the wells and incubated for 1 hour at 37° C. After incubation, wells were blocked with 1% BSA in PBS for 1 hour at room temperature, washed and incubated with the antibody overnight at 4° C. After washing bound antibody was detected with IgG Peroxidase conjugated (Fab specific) for 45 minutes. After washing OPD subtract was added and the color developed was determined by an ELISA reader at 450 nm.

Results a. Isolation of Peptide B (SEQ ID NO 11) and Peptide C (SEQ ID NO 17)

In view of the anti-tumor effect of BAT mAb, it was aimed to select a peptide that binds specifically the antibody from a 12-mer random phage epitope library. After each panning enrichment in the number of plaque forming units (pfu) was observed. Resulting from $1^{st}$ panning a number of $5.6\times10^6$ pfu was obtained, from the $2^{nd}$ one, $2\times10^2$ pfu, after amplification the number of pfu was $2\times10^8$ and after the last round of biopanning $1\times10^3$ pfu were counted (Table 1).

TABLE 1

| Screening for BAT binding peptide. | | | |
|---|---|---|---|
| | Panning 1 | Panning 2 | Panning 3 |
| Number of phages | $2 \times 10^{10}$ | $5.6 \times 10^6$ | $2 \times 10^8$ |
| PFU obtained | $5.6 \times 10^6$ | $2 \times 10^2$ | $2 \times 10^3$ (sequenced 52) |
| Percent (%) | 0.028 | 0.004 | 0.0005 |

DNA from 42 positive clones was sequenced. The DNA from 31 of the phage clones exhibited the sequence:

CAGAGGATACTGCAGCAAATTAATCTTCCCAGGATC (SEQ ID NO 28) encoding for a peptide of SEQ ID NO 11, also termed Peptide B.

The DNA from 3 of the phage clones exhibited the sequence:

AACCGAATCAGGACAAATACTAAGCT-CATGAACAGC (SEQ ID NO 34) encoding for a peptide of SEQ ID NO 17, also termed Peptide C.

The rest of the 8 positive clones exhibited different sequences.

b. Phage ELISA on Anti-M13 Plates.

Figure 5:
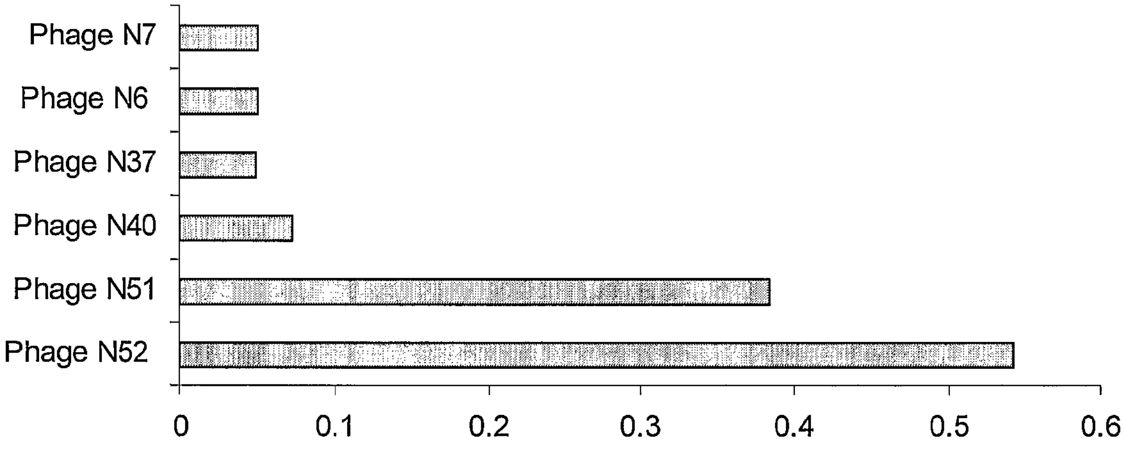
FIG. 5 shows the binding of BAT monoclonal antibody to selected peptides, from the phage-library, in the second experiment.

To ensure that the interaction between the selected phages and BAT mAb is caused by the insert sequences, ELISA on anti M13 binding plates was performed. The ability of the positive phage to bind BAT mAb (5 μg/ml) was assessed. $1\times10^9$ phages from positive pfu were incubated on anti-M13 plates and binding to BAT mAb was assessed. ELISA detected only phages with peptide B in the insert (FIG. 5, phages N51 and N52). Phages with other sequences did not bind to BAT monoclonal antibody (FIG. 5, phages N40, N6, N7, and N37).

Example 3

In Vivo Effect of Peptides

Materials and Methods:

Peptides: Peptide A and Peptide B and variants, are shown in Table 2 (SEQ ID NO 1-17). Peptide were produced by amino-acid synthesis as known in the art.

Mice: C57BL female mice, 6-8 weeks old.

Tumors: B16 syngeneic melanoma cells were inoculated in order to induce the formation of lung metastases. Cells were inoculated i.v. on day 1 following the first peptide injection. Metastases were detected in the lung by their dark coloration, resulting from melanin production in the cells. Tumor growth was monitored by lung weight compared to control mice.

Vaccine composition and dose: A vaccine immunization composed: 10 μg of a peptide and 100 μl of complete Freund's adjuvant (CFA) or PBS.

Vaccination Protocol: C57BL mice were injected with the above dose of peptide vaccine in CFA into the footpads, followed by two boosts of the above dose in PBS on the $7^{th}$ and $14^{th}$ day following the first immunization. Control mice were injected with vehicle alone. BAT (10 μg) monoclonal antibody was injected on day 10 post tumor-inoculation as a positive control. Lung weight was measured on day 24 post tumor inoculation.

Figure 6:
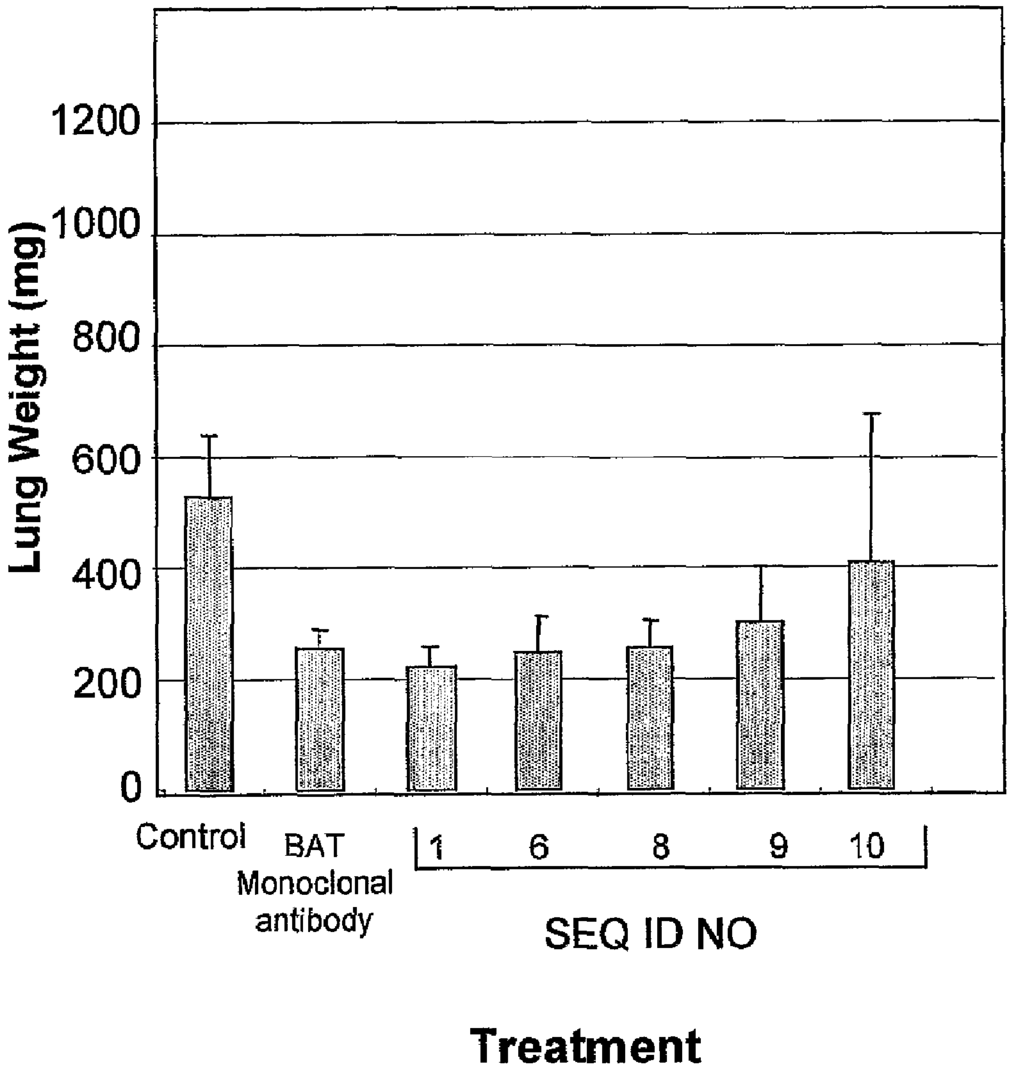
FIG. 6 presents growth inhibition of lung tumors by Peptide A and its analogues.
Figure 7:
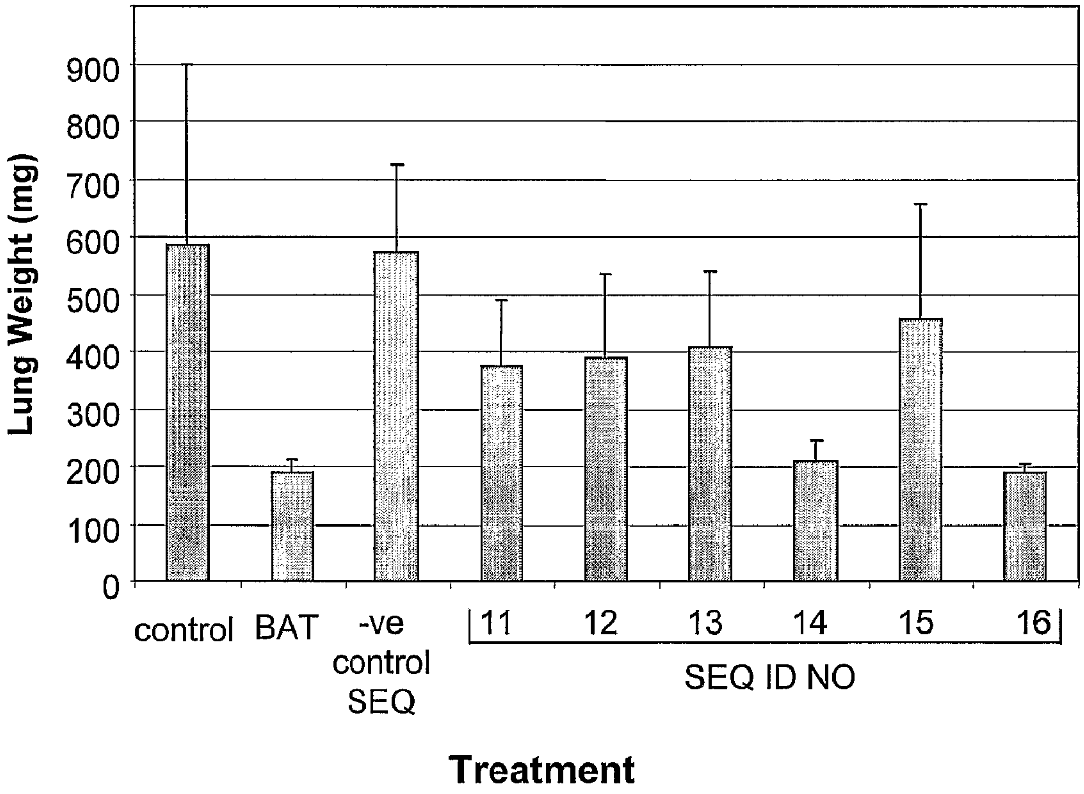
FIG. 7 presents growth inhibition of lung tumors by Peptide B and its analogues.

Results:

Peptide A (SEQ ID NO 1) and several of the variants based on the sequence of Peptide A (SEQ ID NOS 6 and 8-10; FIG. 6) and on the sequence of Peptide B (SEQ ID NOS 14 and 16; FIG. 7) exhibited anti tumor activity similar to that of BAT monoclonal antibody. The anti-tumor activity as a measure of lung weight was approximately twice higher as compared with control (non-treated tumors). Other peptides were found less effective than BAT monoclonal antibody.

TABLE 2

| Peptide analogs | | |
|---|---|---|
| Peptide SEQ ID NO | Peptide sequence | DNA SEQ ID NO |
| 1 (Peptide A) | PRRIKPRKIMLQ | 18 |
| 2 | prrikprkimlq-amide | 18 |
| 3 | PRRFKPRKIBLQ | 19 |
| 4 | PRRIKPRKIBFQ | 20 |
| 5 | PRRIKPRKIBLQ | 21 |
| 6 | PRRIKARKIMLQ | 22 |
| 7 | PRKIKPRKIMLQ | 23 |
| 8 | --RIKPRKIMLQ | 24 |
| 9 | PRRIKPRKIM-- | 25 |
| 10 | acetyl-PRRIKPRKIMLQ | 18 |
| 11 (Peptide B) | QRILQQINLPRI | 26 |
| 12 | QRILQQINLARI | 27 |
| 13 | QRILQEINLPRI | 28 |
| 14 | QRILQQINLPKI | 29 |
| 15 | --ILQQINLPRI | 30 |
| 16 | QRILQQINLP-- | 31 |
| 17 (Peptide C) | NRIRTNTKLMNS | 32 |

Example 4

NK and CTL Cytolytic Activity in Peptide-Immunized Mice

Material and Methods

Cytotoxicity was examined by measuring the release of radiolabeled chromium from target cells. Cells ($2\text{-}4\times10^6$ YAC, B16 or 3LL) were labeled with 200 μCi [$^{51}$Cr]-chromate, in serum free media for 1 h at 37° C. Following three washes, cells were resuspended in complete medium and plated at $10^4$ cells/well. Mouse splenocytes were removed on the indicated days (YAC-day 7, B16 and 3LL-day 21) following peptide immunization. Vaccination regimen was identical to that used in tumor-inhibition experiments (see Example 3). Splenocytes were mixed with target cells at the indicated ratios and incubated for 12 h at 37° C. Supernatants were monitored for radioactivity. Cytotoxicity was determined as follows, $$\%\ \text{Lysis}=100\times(Re-Rs)/R\max-Rs).$$

where Re is the measured release, Rs is the spontaneous release in the presence of medium alone and Rmax stands for the maximal release obtained by incubating target cells with Triton x100. $^{51}$Cr release was determined at effector-to-target cell ratios of 1:5, 1:25 and 1:50.

Results

Figure 8A:
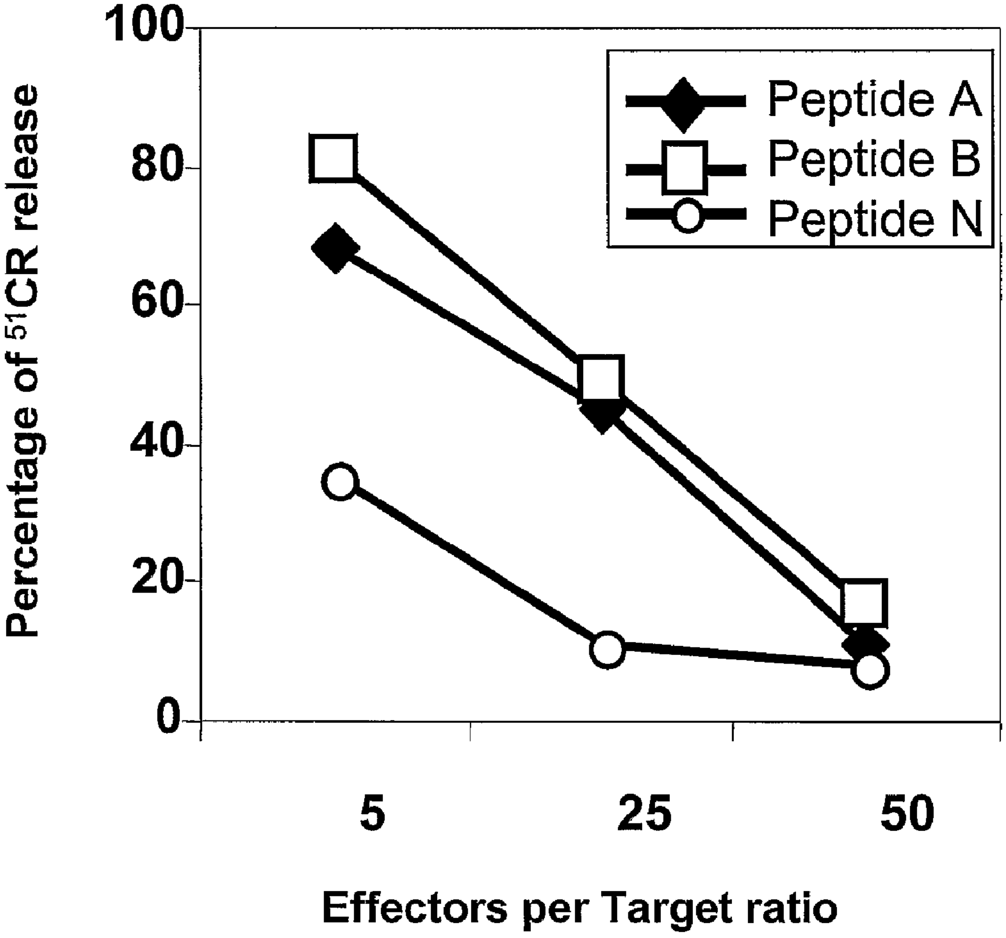
FIGS. 8A, 8B and 8C exhibit cytolytic activity in splenocytes of mice immunized with Peptides A and B.
Figure 8B:
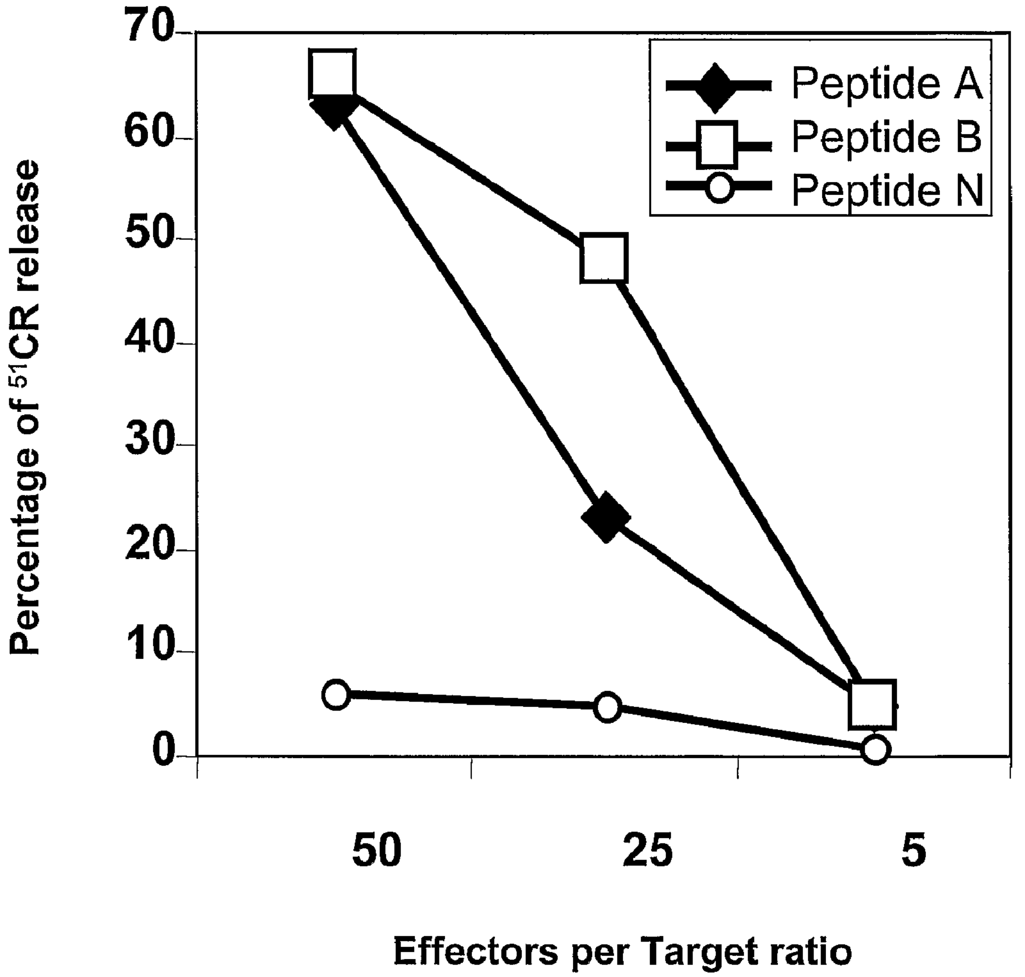
Figure 8C:
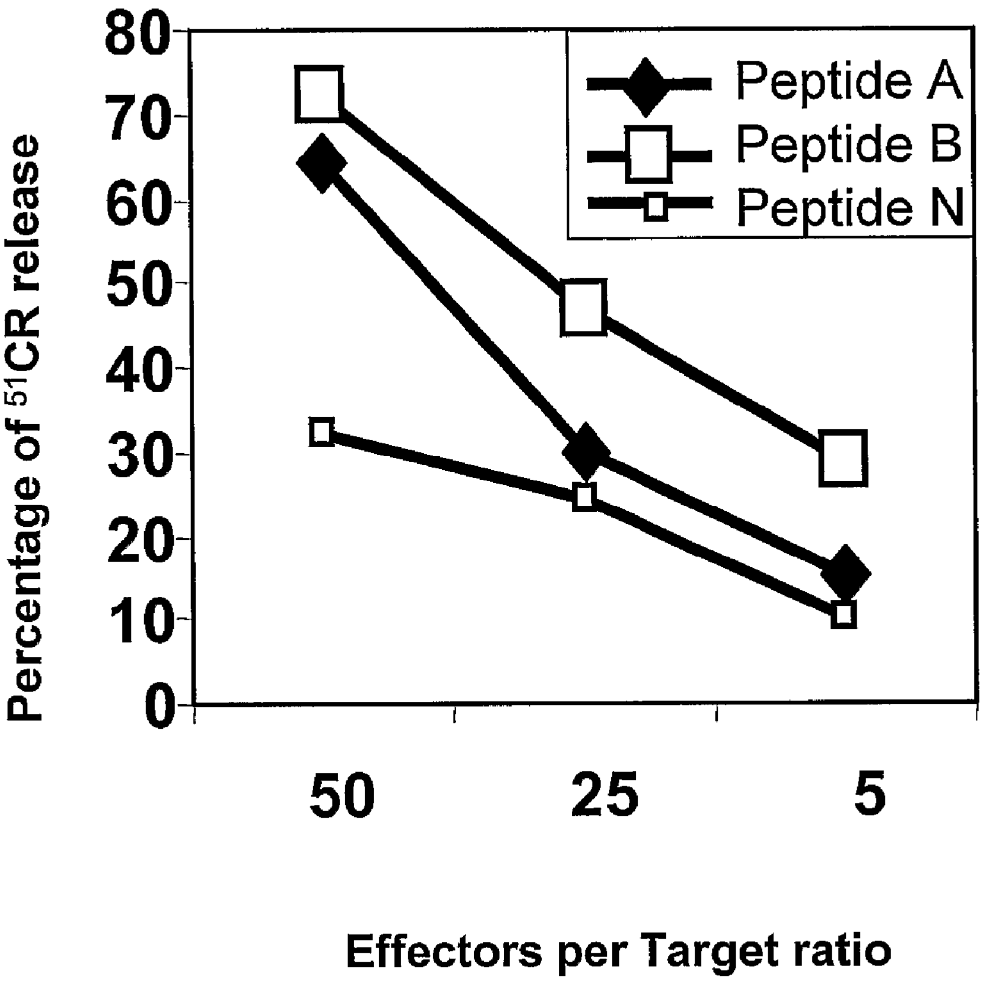
Figure 9A:
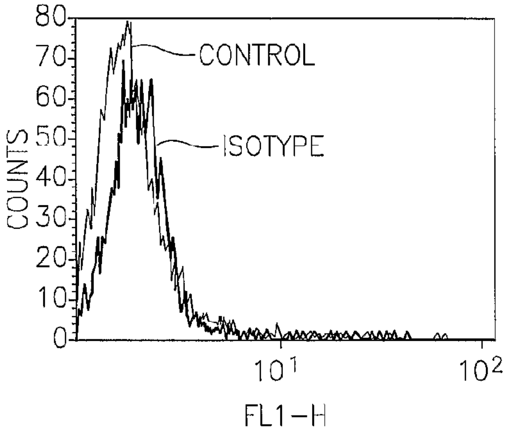
FIGS. 9A-9D show inhibition of BAT monoclonal antibody binding to Daudi cells by anti-Peptides A and B antibodies.
Figure 9B:
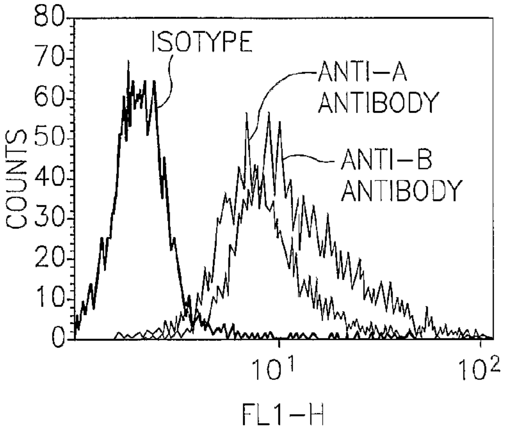
Figure 9C:
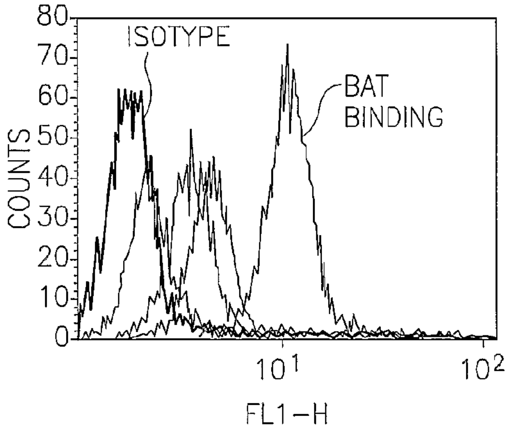
Figure 9D:
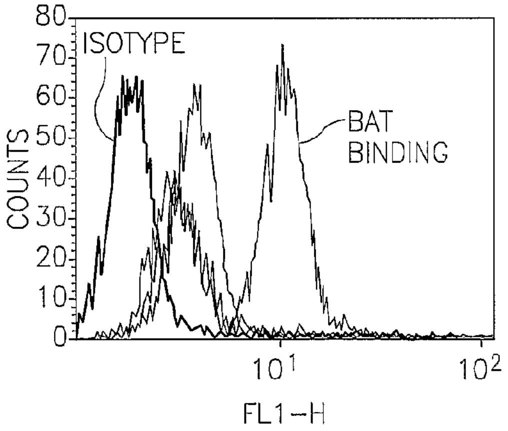

Tumor inhibition by peptide vaccines may depend on both humoral and cellular effects elicited by the immunization. To examine whether peptides A and B induce cellular toxicity, mice immunized with the peptides were studied for their ability to mount tumor-cell lysis in vitro. Following an immunization regimen that elicits an anti-tumor response, splenocyte cytotoxicity against a variety of tumor cells was observed (FIG. 8). Interestingly, this activity was induced against both NK sensitive cells (YAC; FIG. 8A) as well as NK insensitive cells (B16 and 3LL; FIG. 8B and FIG. 8C, respectively), suggesting involvement of both populations in the response. Characteristically, NK-dependent lysis could be observed as early as 7 days following immunization, in accordance with early stimulation of NK cells. NK-independent lysis of B16 and 3LL cells followed a classical time-response of maximal efficacy around day 21.

The above effects could be induced to a similar extent by both peptides A and B, reaching an impressive activity of up to % 80 lysis. Peptide N, a non-relevant control peptide could not elicit a similar response, in accordance with its inability to inhibit tumor growth.

Example 5

Anti-Peptide A and B Antibodies Compete with BAT Monoclonal Antibody Binding to Daudi Cells Materials and Methods:

a. Antibody Purification:

To examine the ability of BAT-selected peptide-vaccines to elicit BAT-like antibodies, serum from peptide-immunized mice was collected and purified on protein-G sepharose beads according to manufacturer's instructions (Pharmacia Corp. NJ, USA).

b. Inhibition of BAT Binding:

Daudi cells ($0.5\times10^6$) were pre-incubated with anti-peptide purified serum, 5, 10 and 20 μg/ml of each purified antibody, for 2 hours on ice. Biotinylated BAT monoclonal antibody (40 μg/ml) was added and cells were incubated for an additional 2 h period at 4° C. Following extensive washing streptavidin FITC was added for 30 minutes. Cells were analyzed by FACScan (Becton Dickinson & Co., NJ, USA). Binding of anti-peptide antibodies alone (20 μg/ml) was determined in a similar manner, however, the detection was performed by incubation with a secondary antibody against mouse IgG conjugated to FITC. In a control sample, cells were exposed only to the secondary antibody.

Results

It is plausible that peptides mimicking the antigenic site of BAT monoclonal antibody can elicit production of antibodies in the serum with similar binding characteristics to those of the original BAT. To examine this possibility, antibodies purified from the serum of peptide-immunized mice were studied for their ability to inhibit the binding of BAT to its antigen (FIG. 9). The binding of anti-A and anti-B antibodies to Daudi cells was verified (FIG. 9B) with respect to control (FIG. 9A), suggesting recognition of BAT antigen.

Determination of BAT binding in the presence of anti-A (FIG. 9C) and anti-B (FIG. 9D) antibodies revealed a common epitope. Both peptides induced mouse antibodies capable of significantly inhibiting BAT binding to its target cells, as demonstrated by the decrease in fluorescent labeling by BAT. This observation is explained by the fact that in the presence of the purified anti-peptide antibodies, BAT antibody could occupy less antigenic determinants on the surface of antigen expressing cells.

Example 6

Anti-Peptide A and B Antibodies Induce Human Lymphocyte Proliferation

Materials and Methods:

a. Human-PBL (Peripheral Blood Lymphocytes) Preparation

Human normal donor blood was diluted 1:1 in PBS. Histopaque (1077-1 SIGMA) was added (1:2 v/v) and the solution was centrifuged for 30 min, 1600 rpm at 4° C. The lymphocyte inter-phase ring was collected, cells washed and incubated in complete media for one hour at 37° C. to remove adherent cells. PBL were collected from supernatant.

b. Thymidine Incorporation

PBL were dispensed at a concentration of $2\times10^6$ cells/ml (200 μl) in 96-well flat-bottom plates in complete medium. BAT or anti-peptide antibodies (1 μg/ml) were added for 5 days followed by incubation in the presence of $^3$[H]Thymidine (1 μCi/well) for 16 h at 37° C. Cells were harvested and radioactivity determined using a liquid B-scintillation counter.

Results

Figure 10:
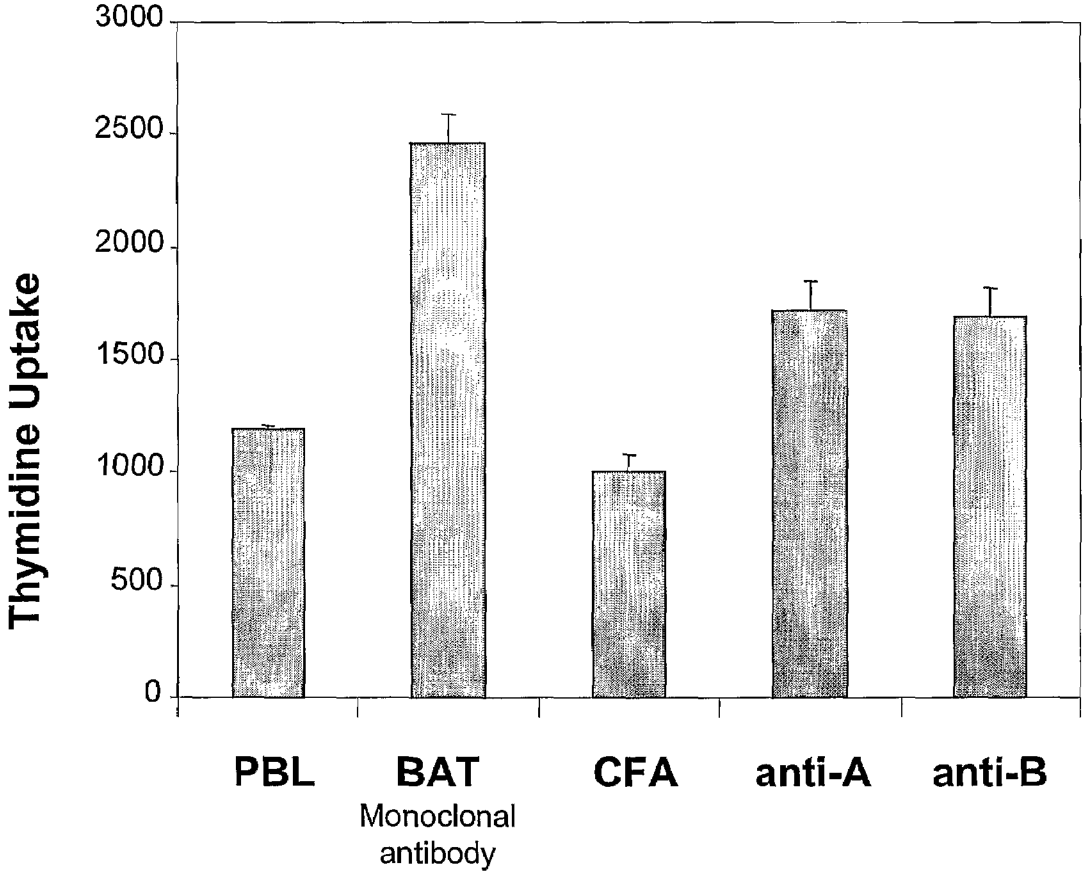
FIG. 10 presents induction of human lymphocyte proliferation by anti-Peptides A and B antibodies.

Human PBL incubated in the presence of antibodies purified from peptide-immunized mice, demonstrated an increased proliferation, similar to that induced by BAT (FIG. 10). These antibodies were effective at a similar concentration and time interval as those of BAT antibody, suggesting a resemblance in efficacy and may be in mechanism. The results suggest that lymphocyte stimulation is correlated with the ability of the vaccine of the invention to elicit an anti-tumor effect. The results further indicate that the antigenic epitope recognized by BAT is involved in lymphocyte activation.

The ability of the peptide-induced antibodies to stimulate lymphocyte proliferation is, most probably, the mechanism underlying their ability to trigger anti-tumor cytotoxicity (as shown in Example 4). In the setting of disease, anti-cancer lymphocytes that are present but beneath a threshold require an efficient immune-response such as the stimulation that is represented by the peptide of the invention in the present example.

Example 7

Peptide Vaccination in Cancer Patients

Vaccination of human subjects with peptides recognized by BAT monoclonal antibody is tested in several studies. The target population for these studies is, in the first case, cancer patients. In these patients, the vaccine is expected to elicit an anti-tumor immune response, allowing to alleviate, reduce, cure or at least partially arrest the disease.

Phase I—Safety study: Double-blind, rising dose, Placebo-controlled.

Phase II—Safety & Efficacy study: Double-blind, rising dose, Placebo-controlled.

Patients who sign informed consent and fulfill inclusion criteria are randomized in a 1:1 ratio to receive the peptide vaccine or placebo (vehicle or adjuvant only). Peptide vaccine and placebo are diluted in sterile saline to generate the administered dosage form. The medication is administered by a suitable route of administration, for example, a fast drip intravenous infusion or peristaltic pump or subcutaneously.

The primary efficacy endpoints of the trial are: the reduction in tumor size, NK and CTL activation, proliferation of lymphocytes and humoral and cellular immune responses to tumor antigens, evaluation of peptide concentration in the blood (pharmacokinetics).

Treatment of cancer patients may exclusively include the peptide vaccine or may include another vaccine comprising a BAT monoclonal antibody. In the latter type of treatment the two vaccines may be administered separately at similar time points or at different time points of the treatment. Safety is assessed by comparing the rate of adverse events, classified according to body system, severity and relation to treatment, between the two groups.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention. Thus the expressions "means to . . . " and "means for . . . ", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same functions can be used; and it is intended that such expressions be given their broadest interpretation.

What is claimed is:

1. An isolated peptide comprising at least one epitope that is recognized by and binds to a BAT monoclonal antibody, said peptide selected from the group consisting of:

(a) a peptide having the sequence of any one of SEQ ID NOs: 3 through 5;

(b) a peptide having at least 90% identity with a peptide of (a); and (c) a combination of peptides according to (a) or (b).

2. The peptide according to claim 1, wherein the peptide has SEQ ID NO 3.

3. The peptide according to claim 1, wherein the peptide has SEQ ID NO 4.

4. The peptide according to claim 1, wherein the peptide has SEQ ID NO 5.

5. An immunomodulating agent comprising the peptide of claim 1.

6. An immunomodulatory vaccine comprising at least one peptide according to claim 1 and a pharmaceutically acceptable adjuvant.

7. The vaccine according to claim 6, wherein the adjuvant is selected from the group consisting of an aluminum salt and an oil in water emulsion.

8. A diagnostic agent for detecting cancer comprising a peptide according to claim 1.

9. A pharmaceutical composition comprising as an active ingredient at least one isolated peptide comprising at least one epitope that is recognized by and binds to a BAT monoclonal antibody, said peptide selected from the group consisting of:

(a) a peptide having the sequence of any one of SEQ ID NOs: 3 through 5;

(b) a peptide having at least 80% identity with a peptide of (a);

(c) a combination of peptides according to (a) or (b); and a pharmaceutically acceptable carrier, excipient or diluent selected from the group consisting of: glucose, mannitol, inositol, sucrose, lactose, fructose, starch, cornstarch, microcrystalline cellulose, hydroxypropylcellulose, hydroxypropyl-methylcellulose, or polyvinylpyrrolidone.

10. The pharmaceutical composition according to claim 9, further comprising one or more of a preservative, a thickener, or a biodegradable polymer.

11. The pharmaceutical composition according to claim 10, wherein the thickener is selected from the group consisting of: a natural gum, a cellulose derivative, or an acrylic or vinyl polymer, and the biodegradable polymer is poly-1,4-butylene succinate, poly-2,3-butylene succinate, poly-1,4-butylene fumarate or poly-2,3-butylene succinate.

12. The pharmaceutical composition according to claim 9, wherein the peptide is present as the pamoate, tannate, stearate or palmitate salt thereof.

13. A method for treating cancer in a subject in need thereof comprising the step of administering a therapeutically effective amount of a composition according to claim 9.

14. A method for treating cancer in a subject in need thereof comprising the step of administering a therapeutically effective amount of a peptide according to claim 1.

* * * * *

SEQUENCE LISTING

```
<160> NUMBER OF SEQ ID NOS: 33

<210> SEQ ID NO 1
<211> LENGTH: 12
<212> TYPE: PRT
<213> ORGANISM: Artificial sequence
<220> FEATURE:
<223> OTHER INFORMATION: recombinant peptide recognized by the BAT-1
      monoclonal antibody

<400> SEQUENCE: 1

Pro Arg Arg Ile Lys Pro Arg Lys Ile Met Leu Gln
1               5                   10


<210> SEQ ID NO 2
<211> LENGTH: 12
<212> TYPE: PRT
<213> ORGANISM: Artificial sequence
<220> FEATURE:
<223> OTHER INFORMATION: recombinant peptide recognized by the BAT-1
      monoclonal antibody
<220> FEATURE:
<221> NAME/KEY: AMIDATION
<222> LOCATION: (12)..(12)

<400> SEQUENCE: 2

Pro Arg Arg Ile Lys Pro Arg Lys Ile Met Leu Gln
1               5                   10


<210> SEQ ID NO 3
<211> LENGTH: 12
<212> TYPE: PRT
<213> ORGANISM: Artificial sequence
<220> FEATURE:
<223> OTHER INFORMATION: recombinant peptide recognized by the BAT-1
      monoclonal antibody

<400> SEQUENCE: 3

Pro Arg Arg Phe Lys Pro Arg Lys Ile Asx Leu Gln
1               5                   10


<210> SEQ ID NO 4
<211> LENGTH: 12
<212> TYPE: PRT
```

-continued

```
<213> ORGANISM: Artificial sequence
<220> FEATURE:
<223> OTHER INFORMATION: recombinant peptide recognized by the BAT-1
      monoclonal antibody

<400> SEQUENCE: 4

Pro Arg Arg Ile Lys Pro Arg Lys Ile Asx Phe Gln
1               5                   10


<210> SEQ ID NO 5
<211> LENGTH: 12
<212> TYPE: PRT
<213> ORGANISM: Artificial sequence
<220> FEATURE:
<223> OTHER INFORMATION: recombinant peptide recognized by the BAT-1
      monoclonal antibody

<400> SEQUENCE: 5

Pro Arg Arg Ile Lys Pro Arg Lys Ile Asx Leu Gln
1               5                   10


<210> SEQ ID NO 6
<211> LENGTH: 12
<212> TYPE: PRT
<213> ORGANISM: Artificial sequence
<220> FEATURE:
<223> OTHER INFORMATION: recombinant peptide recognized by the BAT-1
      monoclonal antibody

<400> SEQUENCE: 6

Pro Arg Arg Ile Lys Ala Arg Lys Ile Met Leu Gln
1               5                   10


<210> SEQ ID NO 7
<211> LENGTH: 12
<212> TYPE: PRT
<213> ORGANISM: Artificial sequence
<220> FEATURE:
<223> OTHER INFORMATION: recombinant peptide recognized by the BAT-1
      monoclonal antibody

<400> SEQUENCE: 7

Pro Arg Lys Ile Lys Pro Arg Lys Ile Met Leu Gln
1               5                   10


<210> SEQ ID NO 8
<211> LENGTH: 10
<212> TYPE: PRT
<213> ORGANISM: Artificial sequence
<220> FEATURE:
<223> OTHER INFORMATION: recombinant peptide recognized by the BAT-1
      monoclonal antibody

<400> SEQUENCE: 8

Arg Ile Lys Pro Arg Lys Ile Met Leu Gln
1               5                   10


<210> SEQ ID NO 9
<211> LENGTH: 10
<212> TYPE: PRT
<213> ORGANISM: Artificial sequence
<220> FEATURE:
<223> OTHER INFORMATION: recombinant peptide recognized by the BAT-1
      monoclonal antibody

<400> SEQUENCE: 9

Pro Arg Arg Ile Lys Pro Arg Lys Ile Met
1               5                   10
```

-continued

<210> SEQ ID NO 10
<211> LENGTH: 12
<212> TYPE: PRT
<213> ORGANISM: Artificial sequence
<220> FEATURE:
<223> OTHER INFORMATION: recombinant peptide recognized by the BAT-1 monoclonal antibody
<220> FEATURE:
<221> NAME/KEY: ACETYLATION
<222> LOCATION: (1)..(1)

<400> SEQUENCE: 10

Pro Arg Arg Ile Lys Pro Arg Lys Ile Met Leu Gln
1               5                   10

<210> SEQ ID NO 11
<211> LENGTH: 12
<212> TYPE: PRT
<213> ORGANISM: Artificial sequence
<220> FEATURE:
<223> OTHER INFORMATION: recombinant peptide recognized by the BAT-1 monoclonal antibody

<400> SEQUENCE: 11

Gln Arg Ile Leu Gln Gln Ile Asn Leu Pro Arg Ile
1               5                   10

<210> SEQ ID NO 12
<211> LENGTH: 12
<212> TYPE: PRT
<213> ORGANISM: Artificial sequence
<220> FEATURE:
<223> OTHER INFORMATION: recombinant peptide recognized by the BAT-1 monoclonal antibody

<400> SEQUENCE: 12

Gln Arg Ile Leu Gln Gln Ile Asn Leu Ala Arg Ile
1               5                   10

<210> SEQ ID NO 13
<211> LENGTH: 12
<212> TYPE: PRT
<213> ORGANISM: Artificial sequence
<220> FEATURE:
<223> OTHER INFORMATION: recombinant peptide recognized by the BAT-1 monoclonal antibody

<400> SEQUENCE: 13

Gln Arg Ile Leu Gln Glu Ile Asn Leu Pro Arg Ile
1               5                   10

<210> SEQ ID NO 14
<211> LENGTH: 12
<212> TYPE: PRT
<213> ORGANISM: Artificial sequence
<220> FEATURE:
<223> OTHER INFORMATION: recombinant peptide recognized by the BAT-1 monoclonal antibody

<400> SEQUENCE: 14

Gln Arg Ile Leu Gln Gln Ile Asn Leu Pro Lys Ile
1               5                   10

<210> SEQ ID NO 15
<211> LENGTH: 10
<212> TYPE: PRT
<213> ORGANISM: Artificial sequence -continued

```
<220> FEATURE:
<223> OTHER INFORMATION: recombinant peptide recognized by the BAT-1
      monoclonal antibody

<400> SEQUENCE: 15

Ile Leu Gln Gln Ile Asn Leu Pro Arg Ile
1               5                   10


<210> SEQ ID NO 16
<211> LENGTH: 10
<212> TYPE: PRT
<213> ORGANISM: Artificial sequence
<220> FEATURE:
<223> OTHER INFORMATION: recombinant peptide recognized by the BAT-1
      monoclonal antibody

<400> SEQUENCE: 16

Gln Arg Ile Leu Gln Gln Ile Asn Leu Pro
1               5                   10


<210> SEQ ID NO 17
<211> LENGTH: 12
<212> TYPE: PRT
<213> ORGANISM: Artificial
<220> FEATURE:
<223> OTHER INFORMATION: recombinant peptide recognized by the BAT-1
      monoclonal antibody

<400> SEQUENCE: 17

Asn Arg Ile Arg Thr Asn Thr Lys Leu Met Asn Ser
1               5                   10


<210> SEQ ID NO 18
<211> LENGTH: 36
<212> TYPE: DNA
<213> ORGANISM: Artificial sequence
<220> FEATURE:
<223> OTHER INFORMATION: nucleotide encoding peptide recognized by the
      BAT-1 monoclonal antibody

<400> SEQUENCE: 18

cctcgacgaa taaagcccag gaagatcatg ctgcaa                               36


<210> SEQ ID NO 19
<211> LENGTH: 36
<212> TYPE: DNA
<213> ORGANISM: Artificial sequence
<220> FEATURE:
<223> OTHER INFORMATION: nucleotide encoding peptide recognized by the
      BAT-1 monoclonal antibody

<400> SEQUENCE: 19

cctcgacgat tyaagcccag gaagatcray ctgcaa                               36


<210> SEQ ID NO 20
<211> LENGTH: 36
<212> TYPE: DNA
<213> ORGANISM: Artificial sequence
<220> FEATURE:
<223> OTHER INFORMATION: nucleotide encoding peptide recognized by the
      BAT-1 monoclonal antibody

<400> SEQUENCE: 20

cctcgacgaa taaagcccag gaagatcray ttycaa                               36


<210> SEQ ID NO 21
<211> LENGTH: 36
```

-continued

<212> TYPE: DNA
<213> ORGANISM: Artificial sequence
<220> FEATURE:
<223> OTHER INFORMATION: nucleotide encoding peptide recognized by the
BAT-1 monoclonal antibody

<400> SEQUENCE: 21
cctcgacgaa taaagcccag gaagatcray ctgcaa 36

<210> SEQ ID NO 22
<211> LENGTH: 36
<212> TYPE: DNA
<213> ORGANISM: Artificial sequence
<220> FEATURE:
<223> OTHER INFORMATION: nucleotide encoding peptide recognized by the
BAT-1 monoclonal antibody
<220> FEATURE:
<221> NAME/KEY: misc_feature
<222> LOCATION: (18)..(18)
<223> OTHER INFORMATION: n=C or T or G or A

<400> SEQUENCE: 22
cctcgacgaa taaaggcnag gaagatcatg ctgcaa 36

<210> SEQ ID NO 23
<211> LENGTH: 36
<212> TYPE: DNA
<213> ORGANISM: Artificial sequence
<220> FEATURE:
<223> OTHER INFORMATION: nucleotide encoding peptide recognized by the
BAT-1 monoclonal antibody

<400> SEQUENCE: 23
cctcgaaaya taaagcccag gaagatcatg ctgcaa 36

<210> SEQ ID NO 24
<211> LENGTH: 30
<212> TYPE: DNA
<213> ORGANISM: Artificial sequence
<220> FEATURE:
<223> OTHER INFORMATION: nucleotide encoding peptide recognized by the
BAT-1 monoclonal antibody

<400> SEQUENCE: 24
cgaataaagc ccaggaagat catgctgcaa 30

<210> SEQ ID NO 25
<211> LENGTH: 30
<212> TYPE: DNA
<213> ORGANISM: Artificial sequence
<220> FEATURE:
<223> OTHER INFORMATION: nucleotide encoding peptide recognized by the
BAT-1 monoclonal antibody

<400> SEQUENCE: 25
cctcgacgaa taaagcccag gaagatcatg 30

<210> SEQ ID NO 26
<211> LENGTH: 36
<212> TYPE: DNA
<213> ORGANISM: Artificial sequence
<220> FEATURE:
<223> OTHER INFORMATION: nucleotide encoding peptide recognized by the
BAT-1 monoclonal antibody

<400> SEQUENCE: 26
cagaggatac tgcagcaaat taatcttccc aggatc 36

-continued

<210> SEQ ID NO 27
<211> LENGTH: 36
<212> TYPE: DNA
<213> ORGANISM: Artificial sequence
<220> FEATURE:
<223> OTHER INFORMATION: nucleotide encoding peptide recognized by the BAT-1 monoclonal antibody
<220> FEATURE:
<221> NAME/KEY: misc_feature
<222> LOCATION: (30)..(30)
<223> OTHER INFORMATION: n=C or T/U or A or G

<400> SEQUENCE: 27
cagaggatac tgcagcaaat taatcttgcn aggatc 36

<210> SEQ ID NO 28
<211> LENGTH: 36
<212> TYPE: DNA
<213> ORGANISM: Artificial sequence
<220> FEATURE:
<223> OTHER INFORMATION: nucleotide encoding peptide recognized by the BAT-1 monoclonal antibody

<400> SEQUENCE: 28
cagaggatac tgcaggarat taatcttccc aggatc 36

<210> SEQ ID NO 29
<211> LENGTH: 36
<212> TYPE: DNA
<213> ORGANISM: Artificial sequence
<220> FEATURE:
<223> OTHER INFORMATION: nucleotide encoding peptide recognized by the BAT-1 monoclonal antibody

<400> SEQUENCE: 29
cagaggatac tgcagcaaat taatcttccc aayatc 36

<210> SEQ ID NO 30
<211> LENGTH: 30
<212> TYPE: DNA
<213> ORGANISM: Artificial sequence
<220> FEATURE:
<223> OTHER INFORMATION: nucleotide encoding peptide recognized by the BAT-1 monoclonal antibody

<400> SEQUENCE: 30
atactgcagc aaattaatct tcccaggatc 30

<210> SEQ ID NO 31
<211> LENGTH: 30
<212> TYPE: DNA
<213> ORGANISM: Artificial sequence
<220> FEATURE:
<223> OTHER INFORMATION: nucleotide encoding peptide recognized by the BAT-1 monoclonal antibody

<400> SEQUENCE: 31
cagaggatac tgcagcaaat taatcttccc 30

<210> SEQ ID NO 32
<211> LENGTH: 36
<212> TYPE: DNA
<213> ORGANISM: Artificial sequence
<220> FEATURE:
<223> OTHER INFORMATION: nucleotide encoding peptide recognized by the BAT-1 monoclonal antibody

<400> SEQUENCE: 32

-continued

```
aaccgaatca ggacaaatac taagctcatg aacagc                            36


<210> SEQ ID NO 33
<211> LENGTH: 36
<212> TYPE: DNA
<213> ORGANISM: Artificial sequence
<220> FEATURE:
<223> OTHER INFORMATION: nucleotide encoding peptide recognized by the
      BAT-1 monoclonal antibody

<400> SEQUENCE: 33

aaccgaatca ggacaaatac taagctcatg aacagc                            36
```